United States Patent [19]

Rajanbabu

[11] Patent Number: 4,912,220

[45] Date of Patent: Mar. 27, 1990

[54] PROCESSES FOR MAKING NITROARYL CARBONYL COMPOUNDS AND NITRODIHYDROARYL CARBONYL INTERMEDIATES THERETO

[75] Inventor: Thaliyil V. Rajanbabu, Wilmington, Del.

[73] Assignee: E. I. Du Pont de Nemours and Company, Wilmington, Del.

[21] Appl. No.: 151,535

[22] Filed: Feb. 3, 1988

Related U.S. Application Data

[62] Division of Ser. No. 3,960, Jan. 16, 1987, Pat. No. 4,743,690, which is a division of Ser. No. 606,631, May 3, 1984, Pat. No. 4,659,862.

[51] Int. Cl.$^4$ ............................................. C07C 87/127
[52] U.S. Cl. .................................... 546/147; 544/380; 544/399; 546/184; 546/185; 546/194; 546/281; 548/127; 549/68; 549/321; 549/499; 560/20; 560/21; 560/23; 568/316; 568/329; 568/331
[58] Field of Search ............................ 560/20, 21, 23; 544/380, 399; 546/147, 184; 549/68, 321, 499; 568/316, 329, 331

[56] References Cited

U.S. PATENT DOCUMENTS

| | | | |
|---|---|---|---|
| 3,547,619 | 12/1970 | Back et al. | 71/111 |
| 3,591,623 | 7/1971 | Back et al. | 260/471 R |
| 3,839,433 | 10/1974 | Wasley | 260/518 R |
| 3,920,839 | 11/1975 | Wasley | 424/319 |
| 3,931,225 | 1/1976 | Fryer et al. | 260/326 N |
| 4,309,424 | 1/1982 | Martin et al. | 424/244 |

OTHER PUBLICATIONS

E. E. Gol'teuzen et al., *Izv. Akad. Nauk. SSSR,* Ser. Khim., No. 5, 1083 (1972).
Hromatka et al., *Monatsh. Chem.,* 100, 469 (1969).
Umio et al., *Chem. Pharm. Bull.* (Tokyo), 17 (3), 605 to 610 (1969).
CA 64: 17522/h.
Germain et al., *J. Heterocyclic Chem.,* 13, 1209 (1976).
Bourdais et al., *Tetrahedron Lett.,* No. 3, 195 (1970).
Garcia et al., *J. Heterocyclic Chem.,* 11, 219 (1974).
Walsh et al., *J. Med. Chem.,* 25, 446 (1982).
Geyer et al., *J. Med. Chem.,* 25, 340 (1982).

*Primary Examiner*—Richard L. Raymond
*Assistant Examiner*—James H. Turnipseed

[57] ABSTRACT

Nitroaryl carbonyl Formula (IIA) compounds, their nitrodihydroaryl carbonyl Formula (I) intermediates, processes for preparing Formula (II) compounds, and a process for preparing Formula (I) compounds, wherein each process comprises the reaction of a nitroaryl compound with a silane.

20 Claims, No Drawings

PROCESSES FOR MAKING NITROARYL CARBONYL COMPOUNDS AND NITRODIHYDROARYL CARBONYL INTERMEDIATES THERETO

RELATED APPLICATIONS

This application is a division of my copending application Ser. No. 07/003,960, filed January 16, 1987, now U.S. Pat. No. 4,743,690, which application is a divisional application of my then copending application Ser. No. 06/606,631, filed May 3, 1984, now U.S. Pat. No. 4,659,862.

BACKGROUND OF THE INVENTION

This invention concerns nitroaryl carbonyl compounds, their intermediate nitrodihydroaryl carbonyl compounds, and processes for preparing the nitroaryl carbonyl and nitrodihydroaryl carbonyl compounds.

There are no known references to nitrodihydroaryl carbonyl compounds. E. E. Gol'teuzen et al., *Izv. Akad. Nauk. SSSR*, Ser. Khim., No. 5, 1083 (1972), discloses related charge-transfer or anionic $\sigma$ complexes derived from 1,3-dinitrobenzene.

Ortho-nitrophenyl and para-nitrophenyl carbonyl compounds are known. Representative of the publications which disclose these types of compounds are: U.S. Pat. No. 3,547,619 (Back); U.S. Pat. No. 3,591,623 (Back); U.S. Pat. No. 3,839,433 (Wasley); U.S. Pat. No. 3,920,839 (Wasley); U.S. Pat. No. 4,309,424 (Martin); U.S. Pat. No. 3,931,225 (Fryer); Hromatka et al., *Monatsh. Chem.*, 100, 469 (1969); Umio et al., *Chem. Pharm. Bull.* (Tokyo), 17 (3), 605 to 610 (1969); and CA 64: 17522/h.

Preparation of certain o-nitrophenyl carbonyl compounds is known. Germain et al., *J. Heterocyclic Chem.*, 13, 1209 (1976), and Bourdais et al., *Tetrahedron Lett.* No. 3, 195 (1970), disclose preparation of some o-nitrophenyl carbonyl compounds by reacting halogen-substituted nitrobenzenes with stabilized carbanion species. Garcia et al., *J. Heterocyclic Chem.*, 11, 219 (1974), disclose preparation of some o-nitrophenyl carbonyl compounds from 2-nitrotoluene by reaction with an acetal of N,N-dimethylformamide followed by acylation and hydrolysis of an intermediate enamine. Walsh et al., *J. Med. Chem.*, 25, 446 (1982), disclose preparation of some o-nitrophenyl carbonyl compounds from substituted o-nitrotoluenes by reaction with diethyloxalate and sodium ethoxide, followed by hydrolysis. Geyer et al., *J. Med. Chem.* 25, 340 (1982), discloses preparation of some o-nitrophenyl carbonyl compounds from 2-(2-nitrophenyl) acetic acids by reaction with benzene in the presence of thionyl chloride and aluminum chloride.

Fused ring nitroaryl carbonyl compounds are very difficult or impossible to prepare by the known processes. Furthermore, none of the known preparations for nitroaryl carbonyl compounds suggests any of the instant processes which comprise reacting a nitroaryl compound with a silane. The processes of the present invention are characterized by being simple to operate and by providing a wide range of products including novel nitrodihydroaryl carbonyl compounds, and novel nitroaryl carbonyl compounds. The nitroaryl carbonyl compounds made by the processes of the instant invention may be converted by conventional chemical methods into useful compounds having pharmaceutical activity.

SUMMARY OF THE INVENTION

This invention concerns nitrodihydroaryl carbonyl compounds of the formula

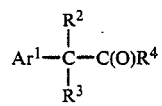

wherein:
$R^2$ and $R^3$, individually, are H, $C_{1-12}$ hydrocarbyl, $C_{2-12}$ heteroacyclic radical or $C_{3-8}$ heterocyclic radical, wherein the heteroatoms are selected from ether oxygen and tertiary nitrogen;
$R^4$ is $C_{1-12}$ hydrocarbyl or $C_{1-12}$ hydrocarbyloxy; or
$R^3$ and $R^4$ can be taken together to form a member of the group $CH_2CH_2O$. $(CH_2)_n$, and $CH_2CH_2N(CH_3)CH_2$ when $R^2$ is H;
n is 4, 5, or 6;
$Ar^1$ is a nitrodihydroaryl radical selected from the group consisting of

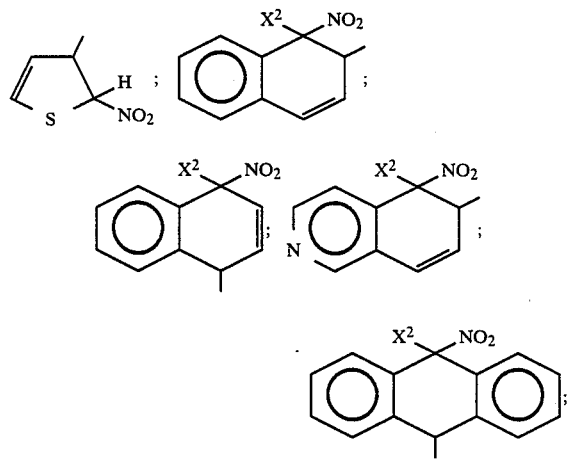

and substituted derivatives thereof, wherein said substituents are inert under reaction conditions;

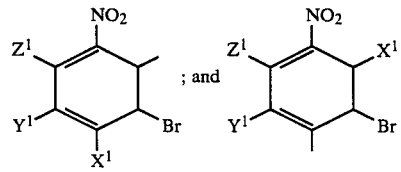

wherein:
$X^2$ is H or Br;
$X^1$, $Y^1$, and $Z^1$ are independently selected from H, F, Cl, Br, $CF_3$, CN, benzoyl, pyridyl, $R^5$, $OR^5$ and $CO_2R^6$; provided that when two or more of $X^1$, $Y^1$, and $Z^1$ are other than H, they are independently selected from F, Cl, Br, $CH_3$, $C_2H_5$, and $OR^7$;
$R^5$ is $C_{1-12}$ hydrocarbyl optionally substituted with Cl, $OCH_3$, or $CO_2R^6$;
$R^6$ is $C_{1-4}$ alkyl; and
$R^7$ is $C_{1-4}$ alkyl.

Preferred Formula (I) compounds are those wherein $Ar^1$ is

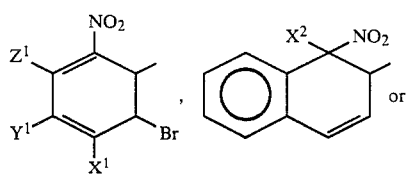 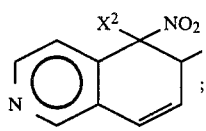

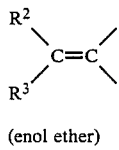

$X^2$, $Y^1$, and $Z^1$ are H; and $X^1$ is H, Cl, or OCH$_3$.

This invention also concerns a process for preparing a nitrodihydroaryl carbonyl Formula (I) compound comprising (a) mixing a nitroaryl compound of the formula ArNO$_2$ with a silane of the formula

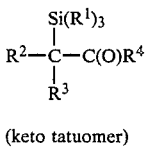

(enol ether)    (keto tautomer)

under anhydrous conditions; (b) cooling the mixture to a temperature below about −20° C.; (c) adding a source of fluoride ion, and (d) adding an electrophilic compound;
wherein:
R$^1$, individually, is C$_{1-4}$ alkyl or phenyl, provided that no more than one of R$^1$ is phenyl;
R$^2$, R$^3$, and R$^4$ are as defined above;
Ar is an aryl radical selected from 2-thienyl; 6-aza-1-naphthyl; 1-naphthyl; 9-anthryl;
and substituted derivatives thereof, wherein said substituents are inert under reaction conditions; and

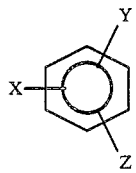

wherein:
X, Y, and Z are independently selected from H, F, Cl, Br, CF$_3$, CN, benzoyl, pyridyl, R$^5$, OR$^5$, and CO$_2$R$^6$; provided that when two or more of X, Y, and Z are other than H, they are independently selected from F, Cl, Br, CH$_3$, C$_2$H$_5$, and OR$^7$; and that when X, Y, and Z are all other than H, one of each of said groups are located ortho, meta and para to NO$_2$, or two of said groups are ortho and one is meta to NO$_2$; and
R$^5$, R$^6$, and R$^7$ are as defined above.

This invention also concerns nitroaryl carbonyl compounds of the formula

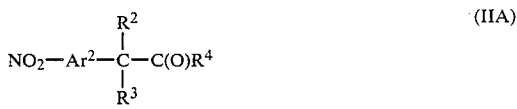

wherein:
R$^2$, R$^3$, and R$^4$ are as defined above; and
Ar$^2$ is a divalent radical selected from the group consisting of

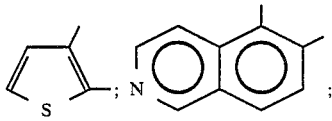

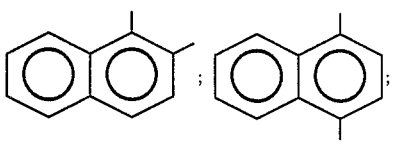

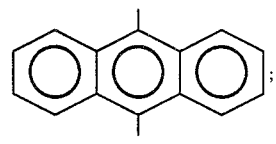

and substituted derivatives thereof, wherein said substituents are inert under reaction conditions.

Preferred compounds of Formula (IIA) are those wherein Ar$^2$ is

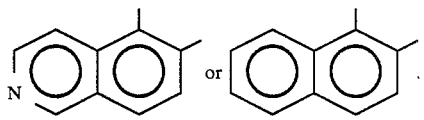

This invention also concerns a process (A) for making a nitroaryl carbonyl compound of the formula

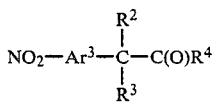

comprising (a) mixing a nitroaryl compound of the formula

Ar'NO$_2$ with a silane of the formula

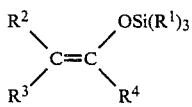

under anhydrous conditions; (b) cooling the mixture to a temperature below about −20° C.; (c) adding a source of fluoride ion; (d) adding bromine as an electrophilic compound; and (e) heating the mixture;
wherein:

$R^1$, $R^2$, $R^3$, and $R^4$ are as defined above; and

Ar' is an aryl radical selected from 6-aza-1-naphthyl; 1-naphthyl; 9-anthryl; and substituted derivatives thereof, wherein said substituents are inert under reaction conditions; and

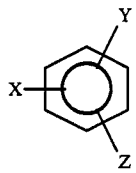

wherein:

X, Y, and Z are independently selected from H, F, Cl, Br, $CF_3$, CN, benzoyl, pyridil, $R^5$, $OR^5$, and $CO_2R^6$; provided that when two or more of X, Y, and Z are other than H, they are independently selected from F, Cl, Br, $CH_3$, $C_2H_5$, and $OR^7$; and that when X, Y, and Z are all other than H, one of each of said groups are located ortho, meta and para to $NO_2$, or two of said groups are ortho and one is meta to $NO_2$; and $Ar^3$ is a divalent radical selected from

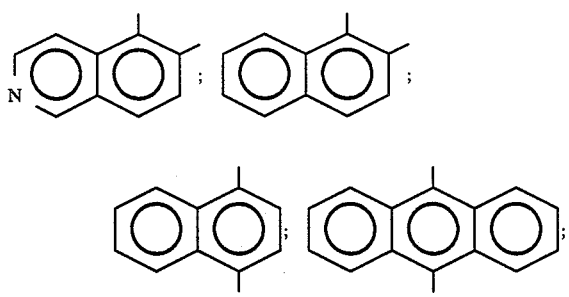

and substituted derivatives thereof, wherein said substituents are inert under reaction conditions;

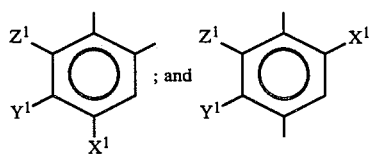

wherein: $X^1$, $Y^1$, and $Z^1$ are as defined above.

This invention also concerns a process (B) for making a nitroaryl carbonyl compound of the formula $$NO_2-Ar^6-\underset{\underset{R^3}{|}}{\overset{\overset{R^2}{|}}{C}}-C(O)R^4 \quad (IIB)$$

comprising (a) mixing a nitroaryl compound of the formula $Ar^4NO_2$ with a silane of the formula

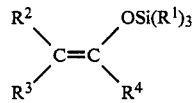

under anhydrous conditions; (b) cooling the mixture to a temperature below about $-20°$ C.; (c) adding a source of fluoride ion; (d) adding a proton source as an electrophilic compound to form an intermediate nitrodihydroaryl carbonyl compound of the formula $$Ar^5-\underset{\underset{R^3}{|}}{\overset{\overset{R^2}{|}}{C}}-C(O)R^4; \quad (IA)$$

(e) isolating the intermediate from the mixture; (f) dissolving the intermediate in a solvent; and (g) treating the intermediate with a quinone;

wherein:

$R^1$, $R^2$, $R^3$, and $R^4$ are as defined above;

$Ar^4$ is a radical selected from 2-thienyl; 6-aza-1-naphthyl; 1-naphthyl; 9-anthryl; and substituted derivatives thereof, wherein said substituents are inert under reaction conditions;

$Ar^5$ is a nitrodihydroaryl radical selected from

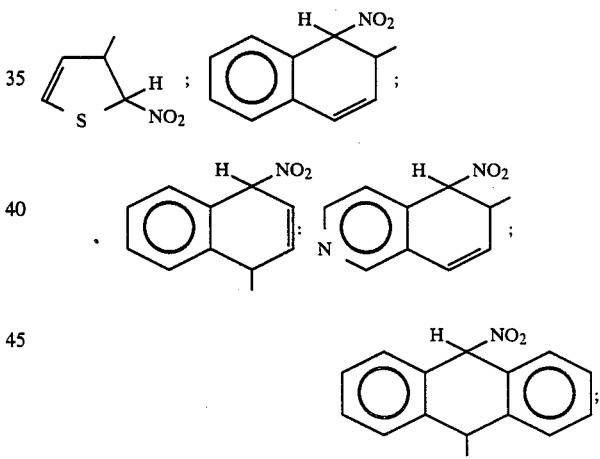

and substituted derivatives thereof, wherein said substituents are inert under reaction conditions; and $Ar^6$ is a divalent nitroaryl radical selected from

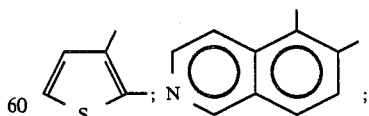

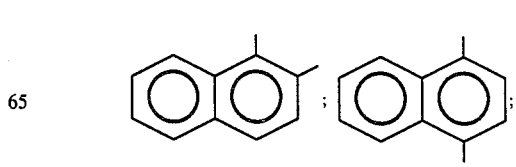

-continued

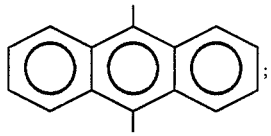

and substituted derivatives thereof, wherein said substituents are inert under reaction conditions.

This invention also concerns a process (C) for making a nitroaryl carbonyl compound of the formula

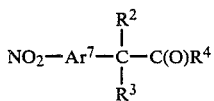  (II)

comprising (a) mixing a nitroaryl compound of the formula $ArNO_2$ with a silane of the formula

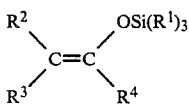

under anhydrous conditions; (b) cooling the mixture to a temperature below about $-20°$ C.; (c) adding a source of fluoride ion; and (d) adding an oxidizing agent; wherein:
$R^1$, $R^2$, $R^3$, $R^4$, and Ar as defined above; and
$Ar^7$ is a divalent radical selected from

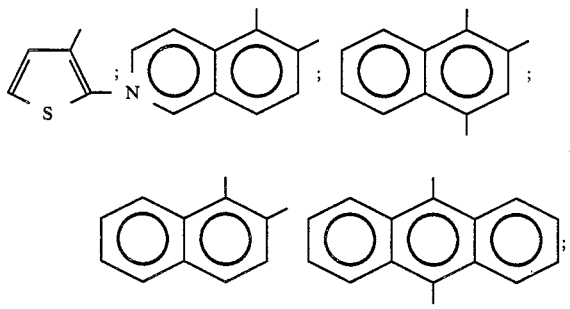

and substituted derivatives thereof, wherein said substitutents are inert under reaction conditions;

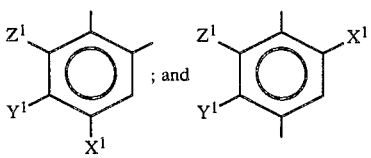

wherein: $X^1$, $Y^1$, and $Z^1$ are as defined above.

It will be clear to one skilled in the art that all Formula (IA) compounds are included within the scope of the Formula (I) compounds, and that all Formula (IA) compounds can be made by the described process for making Formula (I) compounds. It will also be clear to one skilled in the art that all Formula (IIA) and (IIB) compounds are included within the scope of the Formula (II) compounds, and that all Formula (IIA) compounds can be made by the described processes (A) & (C) for making Formula (II) compounds. Additionally, polynuclear Formula (IIA) compounds are included within the scope of the Formula (IIB) compounds, and can be made by the described process (B) for making Formula (IIB) compounds.

By "hydrocarbyl" is meant a monovalent organic group composed solely of carbon and hydrogen, and selected from aliphatic, alicyclic, aromatic, or mixed aliphatic-aromatic.

By "heteroacyclic" is meant an acyclic chain, linear or branched, containing one or more atoms of at least one element other than carbon.

By "heterocyclic" is meant a cyclic moiety containing one or more atoms of at least one element other than carbon within the ring.

By "anhydrous conditions" is meant conditions under which materials are freed from water by normal laboratory drying methods such as distillation and/or treatment with desiccating agents.

By a "source of fluoride ion" is meant a compound which will provide fluoride ions under reaction conditions.

By "electrophilic compound" is meant bromine or a proton source such as water, an acidic salt or an acid.

Preferred nitroaryl starting compounds include nitrobenzene; monosubstituted nitrobenzene, wherein said substituents are selected from $OCH_3$ and Cl; nitronaphthalene and nitroazanaphthalene. Most preferred is nitroazanaphthalene.

Preferred silanes include [(1-methoxy-2-methyl-1-propenyl)oxy]trimethylsilane (MMTS), [(1-methoxy-1-propenyl)oxy]trimethylsilane (MTS), (carbomethoxymethyl)trimethylsilane, and [(oxacyclopent-2-ene-2-yl)oxy]trimethylsilane. MMTS is most preferred.

It should be understood that either silane tautomer represented above may be present alone, or mixed in any proportion with the other tautomer. Hereafter, the silane will be depicted in its enol ether form for the sake of brevity, it being understood that said depiction represents either or both silane tautomers.

DETAILED DESCRIPTION OF THE INVENTION

The aromatic nitro compounds and silane compounds used as starting reactants to make Formula (I) and (II) compounds are known.

Fluoride ion sources operable in the processes of the present invention are known compounds which are at least partially soluble in the solvents employed. Examples of such fluoride ion sources include tris(dimethylamino)sulfonium difluorotrimethylsilicate (TASF) and tetra n-butylammonium fluoride. TASF is a preferred ion source. Preparation of TASF is described by U.S. Pat. No. 3,940,402 (Middleton), ('402 patent), which discloses a class of tris(dialkylamino)sulfonium salts of the general formula

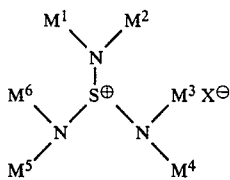

wherein: the M groups are $C_{1-20}$ alkyl wherein each alkyl group has at least two alpha hydrogen atoms, and X includes $(CH_3)_3SiF_2$. The '402 patent also discloses a method for preparing difluorotrimethylsilicate salts of the formula $(M^1M^2N)(M^3M^4N)(M^5M^6N)S^+(CH_3)_3SiF_2^-$, by reacting sulfur tetrafluoride ($SF_4$), dissolved in an anhydrous, inert solvent, with at least 3 mole equivalents of a selected dialkylaminotrimethylsilane.

The electrophilic compounds used in the processes of the present invention include bromine and proton sources; the later include water, acidic salts and acids such as mineral acids and carboxylic acids. Hydrochloric acid and glacial acetic acid are preferred acids. $KH_2PO_4$ and $NaH_2PO_4$ are preferred acidic salts.

In step (a) of the process to prepare the Formula (I) compounds, approximately equimolar amounts of the nitroaryl starting compound and the silane are mixed under anhydrous conditions. Where necessary, a polar aprotic solvent can be added to give a total concentration of about 0.5M to 5M, preferably 0.4M to 1M. Preferred polar aprotic solvents include tetrahydrofuran (THF); acetonitrile; ethers; glycol ethers such as tetraethyleneglycol dimethylether; dimethylformamide; pyridine and mixtures thereof. Most preferably a mixture of THF and acetonitrile is used.

In step (b) of the process to prepare the Formula (I) compounds, the mixture of nitroaryl starting compound and silane is cooled to a temperature below about $-20°$ C., more preferably below $-70°$ C. In step (c), the fluoride ion source, dissolved (1-10M) in a suitable solvent compatible with the reaction mixture, is added slowly (dropwise) with thorough mixing and exclusion of air and moisture, until a molar concentration approximately equal to the nitroaryl or silane compound is present. Preferably, this mixture is stirred for at least 10 minutes. It is preferred that the reaction mixture then be warmed to a temperature of about $-20°$ C. to $0°$ C.; and again stirred for at least 15 minutes, more preferably 30 to 120 minutes. If the electrophilic compound to be added in step (d) is bromine, the reaction mixture should first be cooled again to a temperature below about $-20°$ C., preferably below $-70°$ C.

In step (d) of the process to prepare the Formula (I) compounds, the electrophilic compound is added to the reaction mixture. If the starting nitroaryl compound is nitrobenzene or substituted nitrobenzene, bromine is added in approximately equimolar amount to the other reagents. Preferably, bromine is added as a solution in cyclohexane. If the starting nitroaryl compound is polynuclear, bromine or a proton source such as water, an acidic salt, or an acid, preferably glacial acetic acid, is employed. If the starting nitroaryl compound is nitrothiophene, only a proton source is employed. As previously indicated, bromine must be added at a temperature below about $-20°$ C., preferably below about $-70°$ C., while proton sources may be added at temperatures of $0°$ C. or below. Acidic salts, such as $NaH_2PO_4$, $KH_2PO_4$, or $KHSO_4$, and mineral acids are conveniently used as aqueous solutions. Alternatively, and less preferably, the initial starting reaction mixture containing the nitroaryl compound, silane compound, and fluoride ion source, at a temperature below about $-20°$ C., can be stirred for about 8 to 48 hours, then treated with the electrophilic compound, selected as described above. Reaction pressure is not critical though ambient pressure is preferred.

Formula (I) compounds, wherein $Ar^1$ is polynuclear and $X^2$ is H, or wherein $Ar^1$ is mononuclear, $X^1$ is Br and stability is sufficient such as those prepared in Examples 1, 2, 3 and 8 to 13, can be isolated by warming the mixture containing the Formula (I) compound to room temperature, and then working up by standard procedures. For example, such a standard procedure could entail the addition of water or a saturated aqueous solution of a salt such as sodium bisulfate, extraction of the Formula (I) compound into ether, and evaporation of the ether. Pure samples of the isolated Formula (I) compounds can be obtained by column chromatography on silica.

Certain of the Formula (I) compounds obtained were not isolated, and their structures were inferred from the known structures of the starting nitroaryl compounds, the final nitroaryl carbonyl Formula (II) compounds, and from analytically determined structures of related, isolable compounds of Formula (I). All the Formula (I) compounds are capable of conversion to the nitroaryl carbonyl compounds of Formula (II) with or without intermediate isolation, as Examples 1, 15, and 23 illustrate.

A process (A) is provided for preparing a nitroaryl carbonyl compound of Formula (II). It should be understood that steps (a) to (d) of process (A) are the same as the process to make the Formula (I) compound, with the limitation that the electrophilic compound in step (d) must be bromine. Therefore, after step (d) of process (A), a Formula (I) compound, wherein $Ar^1$ contains bromine, is formed and remains present within the reaction mixture. The bromine-containing Formula (I) intermediate need not be isolated from the reaction mixture prior to effecting step (e) of process (A). In step (e), the reaction mixture is heated to about $-10°$ to $50°$ C. to eliminate HBr and obtain the Formula (II) compound. Alternatively, an amine base can be added to the reaction mixture during step (e) to hasten the formation of the Formula (II) compound. The amine base is preferably a tertiary amine, most preferably triethylamine. More preferably, the Formula (II) compound is obtained by warming the reaction mixture containing the bromine-containing Formula (I) compound from below $-70°$ C. to room temperature. Then, the Formula (II) compound is isolated from the reaction mixture by conventional procedures, preferably by extraction into ether after the addition of water.

In operating step (e) of process (A), it is to be understood that the actual temperature required for the conversion of any given bromine-containing Formula (I) intermediate will depend on its stability. Unisolable Formula (I) compounds will generally be converted at the lower end of the temperature range; i.e. about $-10°$ C. to room temperature. Isolable Formula (I) compounds are more stable, and will generally require higher temperatures for conversion; i.e. about room temperature to $50°$ C., although partial conversion to Formula (II) compounds may occur at temperatures below room temperature.

A process (B) is provided for preparing a nitroaryl carbonyl compound of Formula (IIB). It should be understood that steps (a) to (d) of process (B) are the same as the process to make the Formula (I) compound, with the limitations that the nitroaryl starting compound in step (a) must be thienyl or polynuclear, and the electrophilic compound in step (d) must be a proton source. Therefore, after step (d) of process (B), a Formula (I) compound, wherein $Ar^1$ is polynuclear and $X^2$ is H, is formed. This intermediate nitrodihydroaryl carbonyl compound has been designated as Formula (IA). The Formula (IA) compound is isolated from the reaction mixture in step (e).

In step (f) of process (B), the isolated Formula (IA) compound is dissolved in a solvent. Suitable solvents include aromatic hydrocarbons, preferably toluene, xylene, or benzene. In step (g), the dissolved Formula (IA) compound is treated with a quinone. Suitable quinones include tetrachloro-1,4-benzoquinone, tetrachloro-1,2-benzoquinone and 2,3-dichloro-5,6-dicyano-1,4-benzoquinone. After the Formula (IA) compound is treated with the quinone in step (g), it should be heated to a temperature of about 50° to 150° C., preferably 80° to 100° C., to obtain the Formula (IIB) compound. The Formula (IIB) compound may be isolated by conventional procedures, preferably by extraction into ether after addition of water.

In process (B), the quinone should be present in a molar ratio of about 1.0 to 3 with respect to the intermediate Formula (IA) compound present. The reaction time is dependent on the temperature employed, and may vary from a few minutes to over 24 h. Depending on temperature, time, and type and amount of quinone employed, a denitrified by-product may be formed in addition to the Formula (IIB) compound, said by-product having the formula $$Ar^8-\underset{\underset{R^3}{|}}{\overset{\overset{R^2}{|}}{C}}-C(O)R^4$$

wherein:
$Ar^8$ is

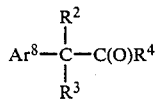

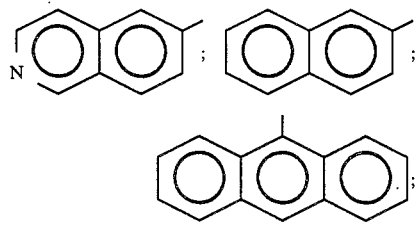

and substituted derivatives thereof, wherein said substituents are inert under reaction conditions; and $R^2$, $R^3$, and $R^4$ are as defined above.

A process (C) is provided for preparing a nitroaryl carbonyl compound of Formula (II) directly, without preparation of the intermediate Formula (I) compound, by forming the mixture containing the nitroaryl starting compound, silane and fluoride ion source, as directed above in steps (a to c) for the preparation of the Formula (I) intermediate. Then, in step (d) of process (C), instead of adding an electrophilic compound, the mixture is treated with a suitable oxidizing agent dissolved in an aprotic solvent at a temperature below about −20° C., preferably below −70° C. The mixture is then heated to about −10° to 50° C., preferably to about room temperature, to obtain the Formula (II) compound. Then, the Formula (II) compound is isolated from the mixture by conventional procedures, preferably by extraction into ether after addition of water.

Oxidizing agents suitable for use in step (d) of process (C) include tetrachloro-1,4-benzoquinone, tetrachloro-1,2-benzoquinone, 2,3-dichloro-5,6-dicyano-1,4-benzoquinone, sulfuryl chloride, sulfuryl bromide and N-bromosuccinimide. When halogens are employed, it may also be beneficial to add an amine during the heating, preferably a tertiary amine.

Suitable aprotic solvents for dissolving the oxidizing agents used in step (d) of process (C) include hydrocarbons such as benzene and toluene; tetrahydrofuran; acetonitrile; ethers including glycol ethers; dimethylformamide; pyridine and mixtures thereof. The dissolved oxidizing agent should be added in at least an equimolar amount with respect to the starting nitroaryl compound present.

While not intending to be bound by any particular reaction mechanism, it is believed that the processes of this invention, wherein the starting nitroaryl compound is converted either directly to the Formula (II) nitroaryl carbonyl compound, or to the intermediate Formula (I) compound, involve the prior formation of transient ionic species which may be illustrated by the following hypothetical equations:

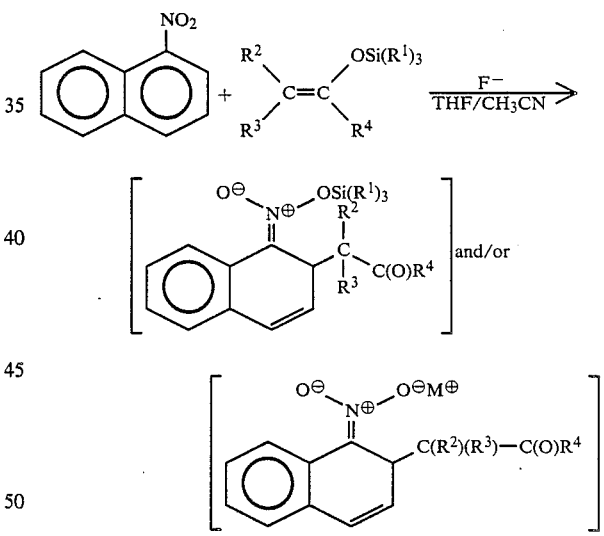

wherein M(+) represents the counterion of the fluoride source; e.g. TAS⊕, and $R^1$, $R^2$, $R^3$ and $R^4$ are as defined above; said transient species being capable of reacting with an electrophilic compound to form the intermediate Formula (I) compound, or with an oxidizing agent to form the nitroaryl carbonyl Formula (II) compound.

The Formula (I) compounds of the present invention are intermediates to the Formula (II) compounds of the present invention, which are intermediates to pharmaceutically active compounds.

The utility of the nitroaryl carbonyl Formula (II) compounds as intermediates to pharmaceutically active compounds is well known. U.S. Pat. No. 3,839,433 (Wasley) and U.S. Pat. No. 3,920,839 (Wasley) disclose p-aminophenyl carbonyl compounds which are prepared by reduction of the corresponding nitrophenyl carbonyl compounds. The disclosed p-aminophenyl carbonyl compounds are pharmaceutically active as both anti-allergic and anti-inflammatory agents. Hromatka et al., *Monatsh. Chem.*, 100, 469 (1969), disclose nitrophenyl carbonyl compounds which are intermediates to benzodiazepin derivatives which are pharmaceutically active as anti-depressant agents. Geyer et al., *J. Med. Chem.*, 25, 340 (1982), disclose other benzodiazepin derivatives useful as anti-depressants which are prepared from nitrophenyl carbonyl compounds. Garcia et al., *J. Heterocyclic Chem.*, 11, 219 (1974), disclose the synthesis of indoles by the reductive cyclization of o-nitrobenzyl carbonyl compounds. Indoles are useful pharmaceutical products. Walsh et al., *J. Med. Chem.*, 25, 446 (1982), disclose reduction of o-nitrobiphenyl and o-nitrophenyl carbonyl compounds to oxindoles which are further converted to 2-aminophenylacetic acid derivatives which are pharmaceutically active as anti-inflammatory agents. Additionally, some nitrophenyl carbonyl compounds are disclosed as intermediates to herbicidally active compounds in U.S. Pat. No. 3,591,623 (Back) and U.S. Pat. No. 3,547,619 (Back).

The nitroaryl carbonyl Formula (II) compound made by the processes of the instant invention may be converted by conventional chemical methods into useful compounds having pharmaceutical activity. For example, when $R^4$ is oxyhydrocarbyl, thus forming an ester group with the adjacent carbonyl radical, the compound may be converted to an aminoarylacetic acid by hydrogenation and hydrolysis, as shown in Utility Examples A and B. Such aminoarylacetic acids produced are known intermediates to pharmaceutical products. Suitable hydrogenating agents include palladium/carbon, alkyl aluminum hydrides, lithium aluminum hydrides, borohydrides and metal-mineral acid mixtures such as Sn/HCl, Fe/acetic acid and 2n/HCl. Aminoarylacetic acids can also be deaminated to the corresponding arylacetic acids by known methods such as treatment with nitrous and hypophosphorous acids. See, for example, "Organic Synthesis", III, 795 (1955); ibid, IV, 947 (1963). Such arylacetic acids produced are known intermediates to pharmaceutical products. Formula II compounds which are o-nitroaryl esters or lactones, when reduced, form oxindoles, as illustrated by Utility Examples C to F. o-nitroaryl lactones can also form hydroxyethyl indoles through selective reduction of keto and nitro functions as illustrated by Utility Example H. o-nitroaryl ketones or aldehydes, when reduced, can form indoles and carbazoles, as illustrated by Utility Example G.

i.e. the direct conversion of starting nitroaryl compounds to Formula (II) and/or (IIA) compounds without intermediate preparation of a Formula (I) compound. Examples 21 to 23, 14, 36 and 37 provide the most preferred procedures for preparing Formula (II) and/or (IIA) compounds. The compound of Example 31 is the most preferred Formula (IIA) compound. The Utility Examples illustrate the conversion of Formula (II) and/or (IIA) compounds to known compounds having pharmaceutical activity. Utility Examples A and B illustrate reduction without cyclization to amines which are intermediate to pharmaceutical compositions. Utility Examples C to F illustrate reductive cyclization to oxindoles. Utility Examples G and H illustrate reductive cyclization to indoles. Example 37 illustrates the synthesis of an anti-inflammation agent.

In the Examples, parts and percentages are by weight. The following abbreviations are used: (dec) - material decomposes at the melting point; UV - ultraviolet absorption; IR - infrared spectroscopy; NMR - nuclear magnetic resonance spectroscopy; HRMS - high resolution mass spectrometry; GC - gas chromatography.

EXAMPLES

The following Examples illustrate the invention. Examples 1 to 14 illustrate the preparation, isolation, and characterization of Formula (I) compounds. Example 3 is the most preferred procedure for preparing Formula (I) compounds. The compounds of Examples 1, 2, 3 and 8 are the most preferred Formula (I) compounds. Example 15 illustrates step (e) of process (A), wherein isolated Formula (I) compounds are converted to the corresponding Formula (II) and/or (IIA) compounds. Examples 16 to 35 illustrate process (A), wherein Formula (II) compounds are prepared from unisolated Formula (I) intermediates. Example 37 illustrates steps (f) and (g) of process (B), i.e. the dissolution and reaction of unbrominated polynuclear Formula (I) compounds with a quinone to form the corresponding Formula (IIB) compounds. Example 36 illustrates process (C),

EXAMPLE 1

Preparation of Methyl α-Methyl-(2-nitro-5-chloro-6-bromocyclohexa-2,4-dien-1-yl)acetate

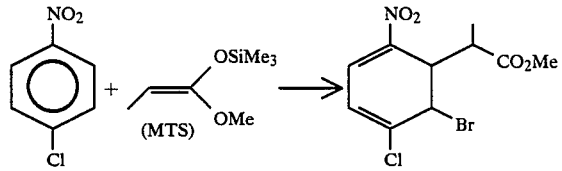

To a solution of 0.779 g (5.00 mmol) of 4-chloronitrobenzene and 0.930 mL (5.04 mmol) of [1-methoxy-1-propenyl)oxy]trimethylsilane (MTS) in 15 mL of anhydrous THF was added 1.348 g (4.90 mmol) of tris(dimethylamino)sulfonium trimethyldifluorosilicate (TASF) in 4 mL of THF and 2 mL of acetonitrile in 10 min at −78° C. The mixture was stirred for 45 min at −78° C. A solution of 0.250 mL (4.88 mmol) of bromine in 2 mL of cyclohexane was added, and the mixture was stirred for 15 min. After warming to room temperature, 20 mL of saturated sodium bisulfite was added. Extraction with four 50 mL portions of ether gave a product mixture from which, after separation by column chromatography, 0.233 g (14%) of the named product was obtained. The following analytical data was obtained: IR (KBr): 1740, 1525, 1345 cm$^{-1}$; $^1$HNMR: δ 7.55 (d, J=6 Hz), 7.48 (d, J=6 Hz) together 1H, 6.30 (d, m, J=6 Hz), 6.34 (d,m,J=6 Hz) together 1H, 5.00 (s, br), 4.90 (s, br) together 1H, 4.15 (d,m,J=5 Hz), 3.97 (d,m,J=5 Hz) together 1H, 3.74 (s), 3.67 (s) together 3H 2.83 (m,1H), 1.22 (d,J=7 Hz), 1.15 (d,J=7 Hz) together 3H; HRMS: M+—HBr,—NO$_2$ 197.0366; calculated for C$_{10}$H$_{10}$O$_2$Cl 197.0369; Chemical ionization mass spectrum: M+ 323 and showed the presence of 1 Cl, 1 Br, and an odd number of N.

EXAMPLE 2

α,α-Dimethyl-(2-nitro-5-chloro-6-bromocyclohexa-2,4-dien-1-yl)acetate

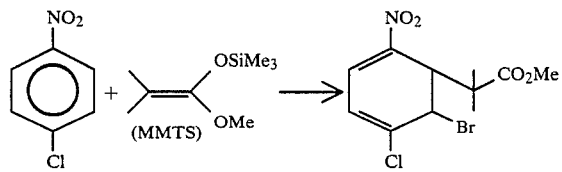

To a mixture of 0.788 g (5 mmol) of 4-chloronitrobenzene and 1.02 mL (5.01 mmol) of [(1-methoxy-2-methyl-1-propenyl)oxy]trimethylsilane (MMTS) in 10 mL of anhydrous THF was added 1.389 g (5.05 mmol) of TASF in 2 mL of acetonitrile and 2 mL of THF at −78° C. The mixture was stirred overnight at −78° C., and then at −20° to −30° C. for 30 min. Subsequently, 0.240 mL (4.70 mmol) of bromine was added, the cold bath was removed, and stirring was continued for 40 min. The products were extracted into ether after adding 20 mL of saturated sodium bisulfite and 20 mL of water. Drying of the aqueous layer, concentration and chromatography on silica gel using 20% ether/hexanes produced the dihydro product in 41% (0.695 g) yield. The melting point was 76 to 77° C. The product material was analyzed by ultraviolet absorption, infrared spectroscopy, nuclear magnetic resonance spectroscopy, and mass spectrometry.

EXAMPLE 3

3-(2-Nitro-5-methoxy-6-bromocyclohexa-2,4-diene-1-yl)-1-(oxacyclopentan-2-one)

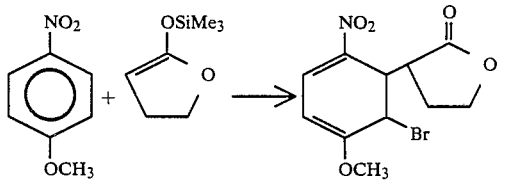

A two-necked flask, fitted with a thermometer and dropping funnel, was charged with 1.53 g (10 mmol) of p-nitroanisole and 2 mL of [(4,5-dihydro-2-furyl)oxy]trimethjylsilane in 30 mL (12 mmol) of anhydrous THF. To the mixture at −78° C. was added 2.75 g (10 mmol) of TASF dissolved in 5 mL of acetonitrile. The mixture was warmed to −15° C., stirred for an hour, and then cooled to −78° C. 0.500 mL (9.7 mmol) of bromine dissolved in 10 mL of cyclohexane was added at below −70° C. After stirring for 15 min at −78° C., the mixture was warmed to room temperature and extracted into ether from the aqueous layer. The combined ether extract was washed with saturated sodium bisulfite and water. Concentration and isolation of the product by column chromatography (1:1 ethyl acetate/hexane:-Silica) yielded 1.25 g (40%) of the named product. The melting point was 138° to 140° C. (dec). The product material was analyzed by ultraviolet absorption, infrared spectroscopy, nuclear magnetic resonance spectroscopy, and mass spectrometry.

EXAMPLE 4

5-[2-Nitro-5-methoxy-6-bromocyclohexa-2,4-dien-1-yl]-2,2-dimethyl-1,3-dioxacyclohexan-4-one

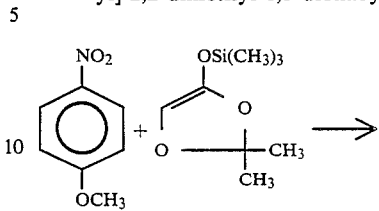

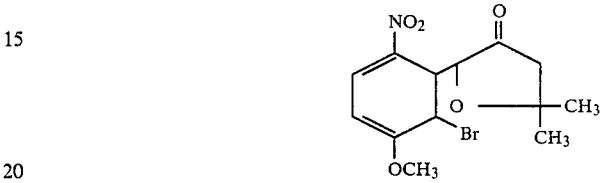

Using the procedure of Example 3 and substituting [(2,2-dimethyl-1,3-dioxacyclopent-4-en-5-yl)oxy]trimethylsilane for the silane of Example 3 will provide the named Formula (1) compound.

EXAMPLE 5

(2,5-Dioxahex-1-yl)α-methyl-[2-nitro-5-methoxy-6-bromocyclohexa-2,4-dien-1-yl]acetate

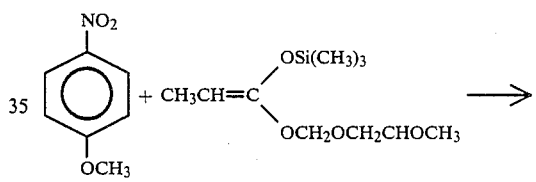

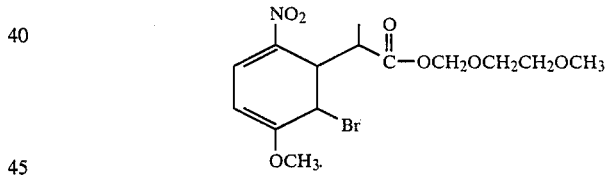

Using the procedure of Example 3 and substituting [(1-[2,5-dioxahex-1-yl)oxy]-1-propenyl)oxy]trimethylsilane for the silane of Example 3 will provide the named Formula (I) compound.

EXAMPLE 6

3-[2-nitro-5-methoxy-6-bromocyclohexa-2,4-dien-1-yl]-1-(N-benzyl)-azacyclohexan-4-one

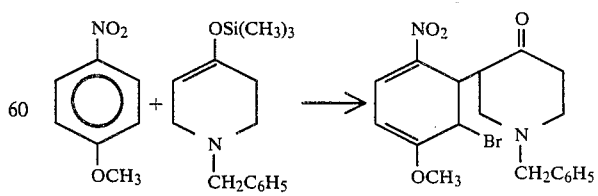

Using the procedure of Example 3 and substituting [(N-benzyl-1-azacyclohex-3-en-4-yl)oxy]trimethylsilane for the silane of Example 3 will provide the named Formula (I) compound.

EXAMPLE 7

Methyl
α-methyl-α-(1,4-diazaphen-2-yl)-[2-nitro-5-ethoxy-6-bromocyclo-hexa-2,4-dien-1-yl]acetate

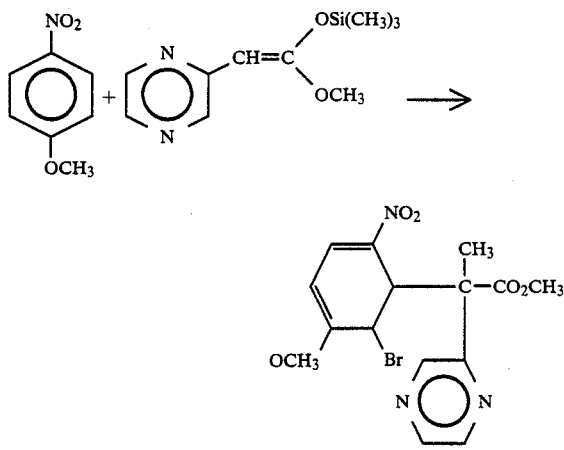

Using the procedure of Example 3 and substituting [(1-methoxy-2-[1,4-diazaphen-2-yl]-1-ethenyl)oxy]-trimethylsilane for the silane of Example 3 will provide the named Formula (I) compound.

EXAMPLE 8

Methyl
α,α-Dimethyl-(2-nitro-5-methoxy-6-bromocyclohexa-2,4-dien-1-yl)acetate

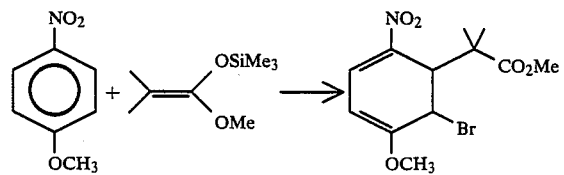

The procedure of Example 3, using MMTS in place of the silane of Example 3, gave 2.313 g (60%) of the above product. The melting point was 115° to 116° C. The product material was analyzed by ultraviolet absorption, infrared spectroscopy, nuclear magnetic resonance spectroscopy, and mass spectrometry.

EXAMPLE 9

Methyl
α-Methyl-1-nitro-1,2-dihydro-6-azanaphthalene-2-acetate

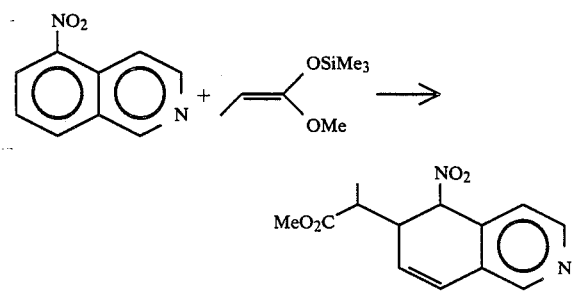

A flame dried 50 mL flask fitted with an addition funnel was charged with 0.872 g (500 mmol) of 5-nitroisoquinoline and 0.95 mL (5.1 mmol) of MTS. An acetonitrile solution of 1.40 g (5.09 mmol) of TASF was slowly added to the reaction mixture in 15 min at −78° C. The mixture was stirred for 22 h at that temperature. One mL of acetic acid in 5 mL of hexane was added, and reaction was warmed to room temperature. After 30 min, 40 mL of water was added. The solid which precipitated out was collected and analyzed. The product yield was 0.972 g (74%). The product material was analyzed by infrared spectroscopy, nuclear magnetic resonance spectroscopy, and mass spectrometry.

EXAMPLE 10

Methyl
α,α-Dimethyl-1-nitro-1,2-dihydronaphthalene-2-acetate

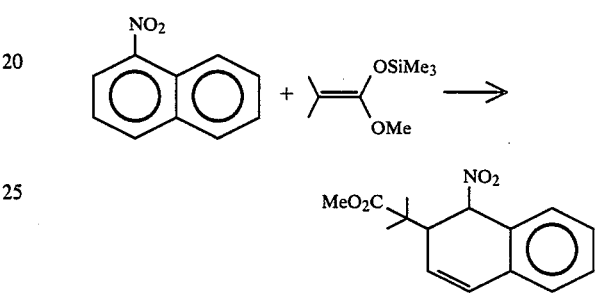

To a solution of 0.833 g (3.03 mmol) of TASF in 10 mL of anhydrous THF and 5 mL of pyridine was added a mixture of 1.732 g (10 mmol) of 1-nitronaphthalene and 2.03 mL (10.20 mmol) of the silyl enolether dropwise at −10° C. The mixture was left to warm to room temperature with the bath in place (3.5 hr). Ten mL of 1N HCl was added, and the mixture was stirred for 5 min. The product was extracted with three 50 mL portions of ether. The combined ether extract was dried, concentrated, and separated chromatographically on silica using 20% ethyl acetate/hexane as solvent. 0.711 g (26%) of the dihydro product was obtained, which was recrystallized from ether/hexanes. The melting point was 74.5° to 76.5° C. The product material was analyzed by ultraviolet absorption, infrared spectroscopy, nuclear magnetic resonance spectroscopy, and mass spectrometry.

EXAMPLE 11

Methyl
α-Methyl-1-nitro-1,2-dihydronaphthalene-2-acetate

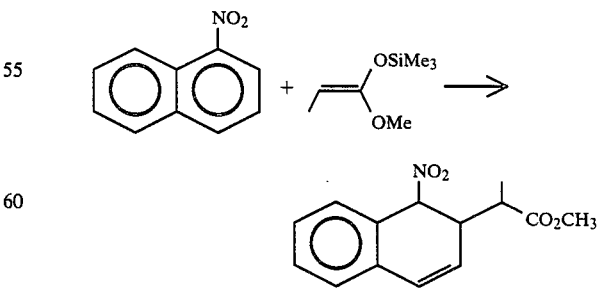

To a solution of 1.737 g (10 mmol) of 1-nitronaphthalene and 1.90 mL (10.28 mmol) of MTS in 25 mL of anhydrous THF was added 2.751 g (10 mmol) of TASF in 10 mL of acetonitrile at −78° C. in 10 min. The mixture was stirred for 22 hrs at −78° C. A mixture of 2 mL of glacial acetic acid and 15 mL of hexane was added at −78° C., followed by 10 mL of saturated potassium hydrogenphosphate. The product was extracted into ether, dried, and concentrated. Column chromatography on silica gel yielded 0.9492 g of pure product as the first fraction. A second, impure fraction after recrystallization from ether/hexane yielded 0.8154 g more of the product. Total yield of crystalline product: 1.765 g (67%). The melting point was 98° C. The following analytical data was obtained: UV (EtOH): 300 (1130), 290 (1530), 258 (8530), 1,2-dihydronaphthalene chromaphore; IR (KBr): 1730, 1600, 1495, 1550, 1360, 1170 cm$^{-1}$; $^1$H NMR (360 MHz) $^1$H NMR (360 MHz): 7.20–7.45 (m, 4H), 6.60 (dd, J=10 Hz, 4 Hz, 1H), 5.90 (d,m, J=10 Hz, 1H), 5.75 (d, J=6.7 Hz, 1H), 3.80 (s, 3H), 3.15 (m, 1H), 2.78 (m, 1H), 1.40 (d, J=7 Hz, 3H); HRMS: (M$^+$—NO$_2$; 215.1036 calculated for C$_{14}$H$_{15}$O$_2$ 215.1082), Analysis revealed carbon, hydrogen and nitrogen.

EXAMPLE 12

Methyl α,α-Dimethyl-9-nitro-9,10-dihydroanthracene-10-acetate

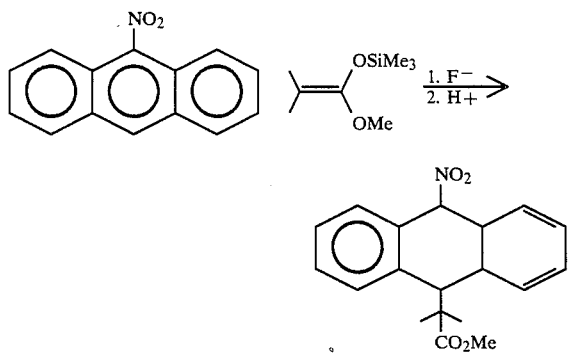

A solution of 1.115 g (5 mmol) of 9-nitroanthracene and 1.01 mL (5 mmol) of MMTS in 20 mL of anhydrous THF was treated with 1.375 g (5 mmol) of TASF dissolved in 3 mL of acetonitrile at −78° C. After addition of TASF had been completed, the reaction mixture was brought to −10° C. and stirred for 1 hr. Ten mL of water was then added, the mixture was warmed to room temperature, and the product was extracted into ether. The organic layer was washed with saturated sodium chloride solution, dried and concentrated. The melting point was 159° to 163° C. (dec). The product material was analyzed by ultraviolet absorption, infrared spectroscopy, nuclear magnetic resonance spectroscopy, and mass spectrometry.

EXAMPLE 13

Methyl α-Methyl-9-nitro-9,10-dihydroanthracene-10-acetate

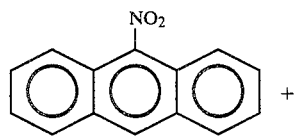

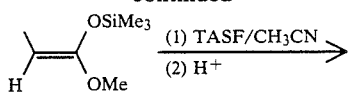

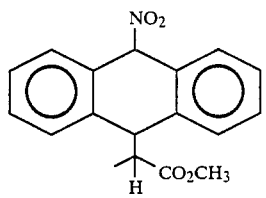

To a solution of 0.757 g (3.39 mmol) of 9-nitroanthracene and 0.663 mL (3.56 mmol) of MTS in 20 mL of anhydrous THF was added 0.941 g (3.42 mmol) of TASF in 2 mL of anhydrous acetonitrile at −78° C. The mixture was stirred for 24 hr. at −78° C. Then, ten mL of saturated KH$_2$PO$_4$ and 20 mL of water were added, the mixture was warmed to room temperature, and the product was extracted into ether. The combined ether extract was washed with water, dried, and concentrated. The major product, 0.491 g (56%), was isolated by column chromatography on silica using 20° ether/hexane as the solvent. Addition of small amount of ether to the major fraction yielded a light yellow solid. The product was analyzed by ultraviolet absorption, infrared spectroscopy, nuclear magnetic resonance spectroscopy, and mass spectrometry.

EXAMPLE 14

Methyl α,α-Dimethyl-2-nitro-2,3-dihydrothiophene-3-acetate

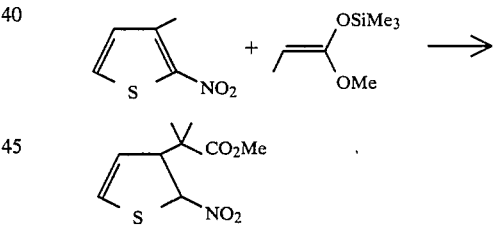

The procedure of Example 9, substituting 2-nitrothiophene (0.646 g, 500 mmol) for 5-nitroisoquinoline, yielded the above product in 31% yield. The product, a viscous oil, was analyzed by infrared spectroscopy, nuclear magnetic resonance spectroscopy, and mass spectrometry.

EXAMPLE 15

Methyl α-Methyl-2-nitro-5-chlorophenyl-1-acetate

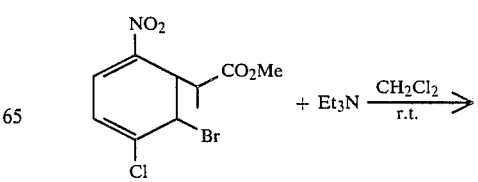

-continued

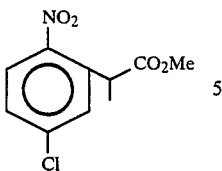

A solution of 0.110 g (0.34 mmol) of methyl 2-(2-bromo-3-chloro-6-nitro-1,2-dihydrophenyl)propionate, prepared as in Example 1, in 3 mL of $CH_2Cl_2$, was stirred with 0.100 mL of triethylamine for 4 h. Thin layer chromatography showed presence of trace amounts of starting material and the expected product. Fifteen mL of 25N HCl was added followed by 40 mL of methylene chloride. The organic phase was separated and washed with saturated sodium chloride and water. Concentration gave 0.083 g (100%) of the dehydrobomination product, in oil, identifed by G.C. and $^1H$ NMR spectroscopy.

EXAMPLE 16

Methyl α,α-Dimethyl-4-nitrophenyl-1-acetate

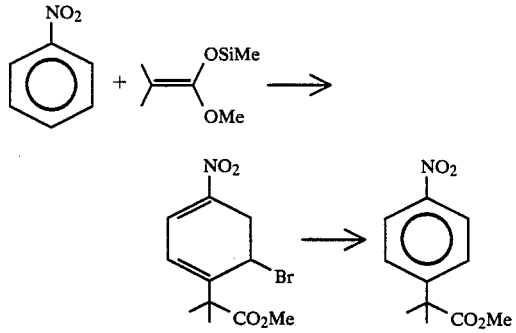

A. To a mixture of 1.02 mL (10 mmol) of nitrobenzene and 2.14 mL (10.75 mmol) of MMTS in 15 mL of THF was added 2.751 g of TASF dissolved in 5 mL of acetonitrile. The dropping funnel containing the TASF solution was washed down with 5 mL of THF. The cold bath was removed, and the reaction was warmed to −10° C. and maintained at −10° C. for 1 hr. After being cooled to −78° C., 0.512 mL (10 mmol) of bromine in 2 mL of cyclohexane was added dropwise. The cold bath was removed, and the mixture was brought to room temperature. Stirring was continued for 1 hr. Twenty mL of saturated sodium bisulfite was added, and the product was extracted into ether. Isolation by chromatography on silica gel yielded 1.824 g (79%) of the para adduct identified by infrared spectroscopy, nuclear magnetic resonance spectroscopy, and high resolution mass spectroscopy.

B. To a mixture of 1.02 mL (10 mmol) of nitrobenzene and 2.40 mL (12 mmol) of MMTS in 10 mL of THF was added 10 mL (10 mmol) of 1N solution of tetra-n-butylammonium fluoride. The mixture was warmed to −10° to −20° C. and stirred for 1 hr. It was subsequently cooled to −78° C. and 0.51 mL (10 mmol) of bromine in 10 mL of cyclohexane was added. The cold temperature bath was removed, and 30 mL of saturated sodium bisulfite was added. Extraction with ether and isolation of the product by standard techniques yielded 0.576 g (26%) of product identified by comparison of spectral properties with those of the product of Part A.

EXAMPLE 17

Methyl α-Methyl-2- and 4-nitrophenyl-1-acetates

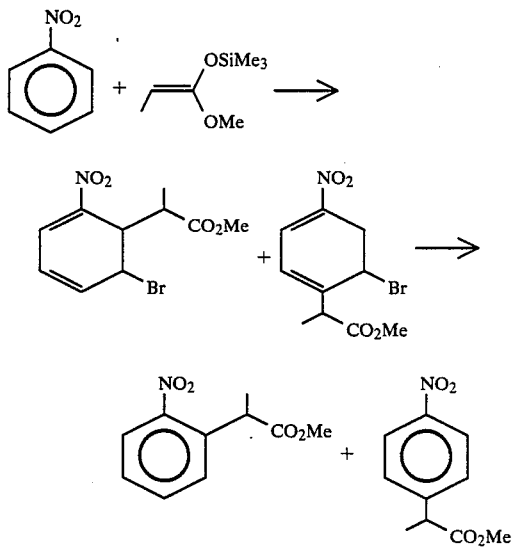

To a solution of 5.11 mL (40 mmol) of nitrobenzene and 9.69 mL (52.5 mmol) of MTS in 85 mL of anhydrous THF was added 13.755 g (50 mmol) of TASF in 15 mL of anhydrous acetonitrile, and 15 mL of THF at a rate such that the temperature did not exceed −75° C. The last traces of TASF were washed down from the dropping funnel with 2 mL of acetonitrile. The mixture was stirred at −78° C. for 21 hrs, and subsequently treated with 2.5 mL (48.81 mmol) of bromine in 10 mL of cyclohexane. After 15 min at −78° C., the mixture was warmed to room temperature and stirred for 1 hr. Fifty mL of saturated aqueous $KH_2PO_4$ solution was added, and the product was extracted into four 100 mL portions of ether. The ether extract was washed with saturated sodium chloride, dried, and concentrated. Sublimation in a Kugelrohr oven gave 5.46 g (52%) of a mixture of o- and p-adducts in a ratio of 7:3 as determined by gas chromatography (3% SE30, 6'×18" glass column, 130° C.). Complete separation of the two compounds by column chromatography was not possible. Both the o and p product materials were analyzed by ultraviolet absorption, infrared spectroscopy, nuclear magnetic resonance spectroscopy, and mass spectrometry.

EXAMPLE 18

Methyl 2- and 4-Nitrophenylacetates

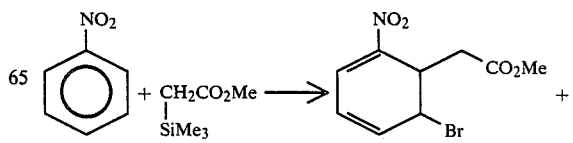

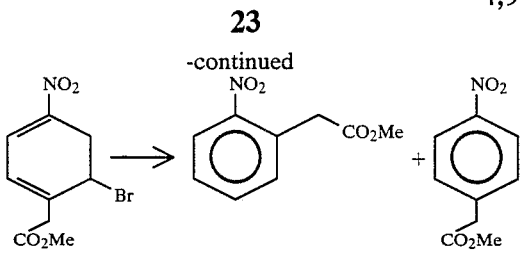

A mixture of 5.11 mL (50 mmol) of nitrobenzene and 8.63 mL (52.5 mmol) of (carbomethoxymethyl)trimethylsilane in 100 mL of THF was treated with 13.75 g (50 mmol) of TASF dissolved in 15 mL of acetonitrile and 15 mL of THF at −78° C. The mixture was stirred for 20 hrs. at −78° C., and then 2.50 mL (50 mmol) of bromine in 10 mL of cyclohexane was added. After stirring at −78° C. for 10 min, the mixture was warmed to room temperature. Fifty mL of saturated sodium bisulfite was added, and the product was extracted into ether. The ether extract was washed with saturated sodium chloride, dried, and concentrated. Chromatography on silica using ether/hexanes yielded 4.16 g (48.6%) of product identified as a mixture of o- and p-adducts by comparing them with authentic samples of methyl-2-nitrophenylacetate and methyl-4-nitrophenylacetate on G.C. The ratio of ortho:para was 55/45, as determined by G.C. and NMR.

EXAMPLE 19

3-(2-Nitrophenyl)oxacyclopentan-2-one;

3-(4-Nitrophenyl)oxacyclopentan-2-one

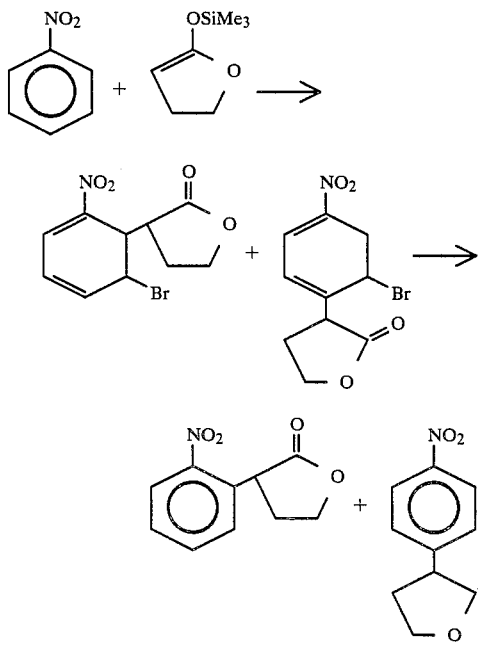

A solution of 2.75 g (10 mmol) of TASF in 3 mL of acetonitrile and 3 mL of THF was added to a solution of 1.02 mL (10 mmol) of nitrobenzene and 1.93 mL (10.50 mmol) of [(oxacyclopent-2-ene-2-yl)oxy]trimethylsilane (OCS) in 12 mL of anhydrous THF at −78° C. over 10 min. The last traces of TASF from the dropping funnel were washed down with additional 5 mL of THF. The mixture was stirred for 20 hrs. at −78° C. Then, 0.460 mL (8.98 mmol) of bromine was added from a dropping funnel. The mixture was stirred at −78° C. for 15 min, and then the cold bath was removed. Stirring was continued for 1 hr. Thirty mL of freshly prepared saturated sodium bisulfite was added, and the product was extracted into four 60 mL portions of ether. Combined ether extracts were washed with saturated potassium hydrogen phosphate and sodium chloride. Concentration and chromatography on silica yielded two products identified as the ortho and para addition products. The ortho-adduct yielded 0.660 g (32%) of product which had a melting point of 112°–117° C. (dec). The para-adduct yielded 0.282 g (14%) of product which had a melting point of 76° to 78° C. Both the o- and p-products were analyzed by ultraviolet absorption, infrared spectroscopy, nuclear magnetic resonance spectroscopy, and mass spectrometry.

EXAMPLE 20

3-(5-Chloro-2-nitrophenyl)oxacyclopentan-2-one

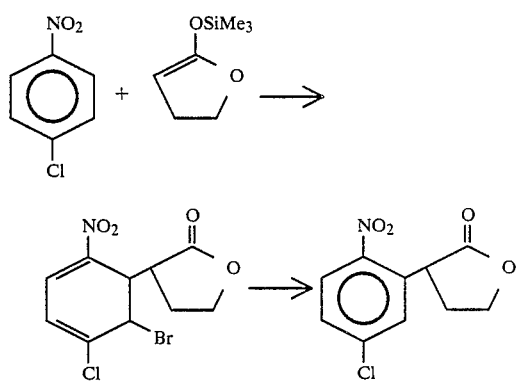

By the procedure outlined in Example 16, 4-chloronitrobenzene was substituted for nitrobenzene and yielded 55% of the corresponding nitrophenyl lactone product with a melting point of 93° C. The product was analyzed by ultraviolet absorption, infrared spectroscopy, nuclear magnetic resonance spectroscopy, and mass spectrometry.

EXAMPLE 21

2-(2-Nitro-5-chlorophenyl)cyclohexanone

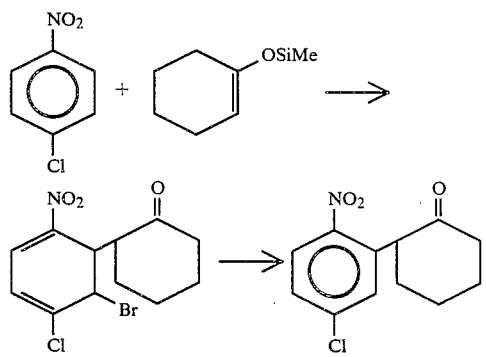

To a mixture of 1 mL (5.33 mmol) of (1-cyclohexene)oxytrimethylsilane and 0.788 g (5 mmol) of 1-chloro-1-nitrobenzene in 20 mL of THF, in a 100 mL flask fitted with an addition funnel, was added 1.375 g (5 mmol) of TASF at −78° C. A solution (acetonitrile/THF: 5 mL/5 mL) of TASF was added dropwise over 10 min. The mixture was stirred overnight at −78°

C. At −78° C., 0.250 mL (5 mmol) of bromine was added dropwise, and the mixture was warmed to room temperature. Two equivalents (1.40 mL) of triethylamine were then added, and the reaction mixture was stirred for 1 hr. Addition of sodium bisulfite, and extraction into ether yielded the crude product containing the starting material and expected product. The product was isolated by column chromatography which produced a 0.632 g (50%) product yield. The product, an oil, was analyzed by ultraviolet absorption, infrared spectroscopy, nuclear magnetic resonance spectroscopy, and mass spectrometry.

EXAMPLE 22

Methyl α-Methyl-2-nitro-5-chlorophenyl-1-acetate

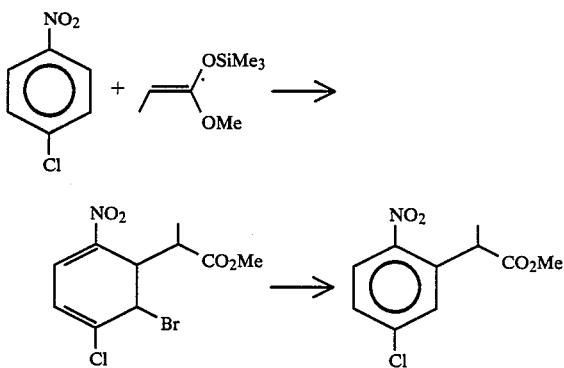

Into a flame-dried, 100 mL three-necked flask were taken 0.788 g (5 mmol) of 4-chloro-1-nitrobenzene and 1.12 mL (5.5 mmol) of MTS in 10 mL of THF. From an addition funnel was added 1.3617 g (4.95 mmol) of TASF in approximately 5 mL of THF and 5 mL of acetonitrile at −78° C. The mixture was stirred in a cold bath at −78° C. for 22 hrs. A solution of 0.25 mL (4.9 mmol) of bromine in 4.5 mL of acetonitrile was added, and stirring was continued for 10 min at −78° C. Cold bath was removed and 1.40 mL (10 mmol) of triethylamine was added in 10 min. Stirring was continued for 1 hr. Thirty mL of saturated sodium bisulfite was added, and the product was extracted with four 50 mL portions of ether. Combined ether extract was washed with 30 mL of 1N HCl and 30 mL of water, and then dried over anhydrous magnesium sulfate. The drying agent was filtered off, and the product was isolated by concentration and column chromatography on silica using 20% ether/hexanes which produced a 0.698 g (50%) product yield. The product was an oil. The following analytical data was used to determine the product's structure as depicted above: IR (neat): 1740, 1525, 1350 cm$^{-1}$; $^1$H NMR: δ1.60 (d, J=6 Hz, 3H), 3.63 (s, 3H), 4.33 (q, J=6 Hz, 1H), 7.40 (d,d,J=8,2 Hz, 1H), 7.46 (s, 1H), 7.93 (d, 8 Hz, 1H); HRMS: 197.0355, (M+—NO$_2$; calculated for C$_{10}$H$_{10}$O$_2$ 197.0369), 184.0161 (M+—CO$_2$Me; calculated 184.0165).

The reaction was also carried out at −10° to −20° C., with stirring for 3 hrs, followed by bromine addition at −78° C., and warming to room temperature. The yield was approximately 50%.

EXAMPLE 23

2-(2-Nitro-4-chlorophenyl)-1-phenylethanone

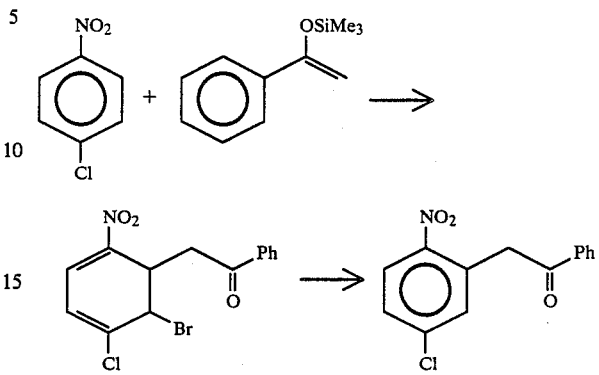

To a solution of 1.5858 g (10 mmol) of 4-chloronitrobenzene in 2.01 g (10.46 mmol) of [(1-phenyl-1-ethenyl)oxy]trimethylsilane in 20 mL of anhydrous THF was added 2.7024 g (9.83 mmol) of TASF in 5 mL of acetonitrile and 5 mL of THF at −78° C. The mixture was stirred overnight (17 hrs) at −78° C., and from a syringe, 0.450 mL (8.8 mmol) of bromine was added at −78° C. The mixture was stirred for 15 min at −78° C., and subsequently was warmed up to room temperature in 1 hr. After stirring for 1 hr, 40 mL of saturated aqueous sodium bisulfite was added, and the product was extracted with ether. The organic phase was dried, concentrated, and evaporated to get crude product which was purified by column chromatography on silica using 30% ethyl acetate and hexane. The yield was 1.0150 g (35%) of product. The product was recrystallized from ether, and had a melting point of 120° to 121° C. The product was analyzed by ultraviolet absorption, infrared spectroscopy, nuclear magnetic resonance spectroscopy, and mass spectrometry.

EXAMPLE 24

Methyl 2-(2-Nitro-5-chlorophenyl)acetate

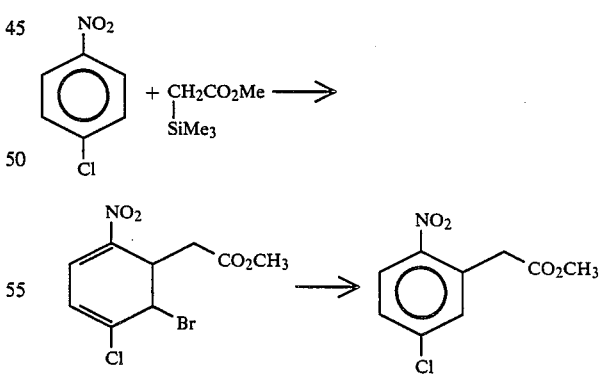

To a solution of 1.576 g (10 mmol) of 4-chloronitrobenzene and 1.68 mL (10.22 mmol) of carbomethyoxymethyltrimethylsilane in anhydrous THF was added 2.751 g (10 mmol) of TASF in 5 mL of acetonitrile at −78° C. The mixture was stirred for 7 hrs at that temperature, and 0.50 mL (9.70 mmol) of bromine was added dropwise. Stirring was continued for 1 hr, and saturated sodium bisulfite was added. The product was extracted into ether and isolated by chromatography on silica using 30% ether/hexane as solvent. The yield was 1.15 g (50%) product, which was an oil. The product was analyzed by infrared spectroscopy and nuclear magnetic resonance spectroscopy.

EXAMPLE 25

Methyl α-Methyl-2-nitro-3,5-dichlorophenyl-1-acetate

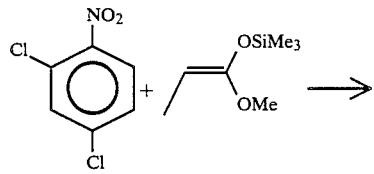

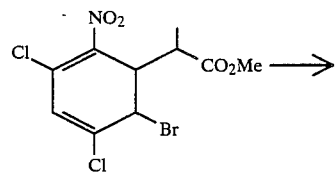

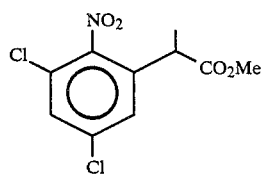

A solution of 5.502 g (20 mmol) of TASF in 6 mL of acetonitrile was added to a solution of 3.84 g (20 mmol) of 2,4-dichloronitrobenzene and 3.88 mL (21 mmol) of MTS in 50 mL of anhydrous THF at −78° C. The mixture was stirred at −78° C. for 2.5 hrs, and 1 hr at −40° C. The mixture was then cooled again to −78° C., and 1.02 ml (19.90 mmol) of bromine in 30 mL of dioxane was added in 20 min. The cold bath was removed, 30 mL of saturated sodium bisulfite solution was added, and the product was extracted into ether. The organic layer was dried and concentrated. Chromatography on silica gel yielded 2.132 g (46%) of the desired product, which was an oil. The product was analyzed by gas chromatography infrared spectroscopy, nuclear magnetic resonance spectroscopy, and mass spectrometry. Gas chromatography/mass spectroscopy showed a complete absence of any dechlorinated product.

The reaction was also carried out at −10° C. with stirring for 1 hr and yielded 61% product.

EXAMPLE 26

Methyl α-Methyl-2-nitro-5-methylphenyl-1-acetate

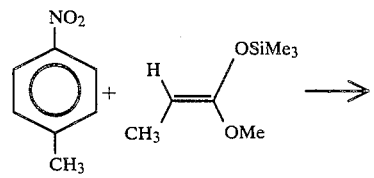

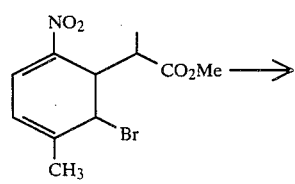

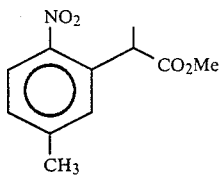

To a mixture of 1.403 g (10.23 mmol) of 4-nitrotoluene and 2.08 mL (11.13 mmol) of MTS in 10 mL of anhydrous THF was added 0.872 g (3.17 mmol) of TASF dissolved in 5 mL of acetonitrile at −30° C. The mixture was stirred at −30° C. for 3 hrs at −78° C. The 0.51 mL (9.95 mmol) of bromine was added, and stirring was continued for 15 min. Cold bath was removed and 2.80 mL (20 mmol) of triethylamine was added. After 1 hr, 30 mL of saturated sodium bisulfite was added and the product was extracted into ether. Chromatography of the crude product yielded 0.481 g (44%) of product, which was an oil. The product was analyzed by ultraviolet absorption, infrared spectroscopy, and mass spectrometry.

EXAMPLE 27

3-(2-Nitro-5-methylphenyl)oxacyclopentan-2-one

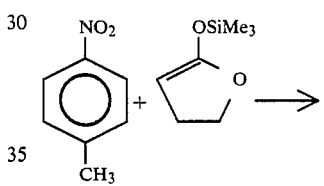

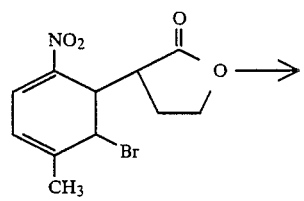

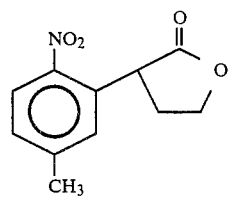

To a solution of 1.372 g (10 mm) of 4-nitrotoluene and 2 mL (10.05 mmol) of OCS in 30 mL THF, was added 2.751 g (10 mmol) of TASF in 10 mL of acetonitrile at −78° C. The mixture was warmed to −15° to −20° C., and stirred at that temperature for 1 hr. After cooling to −78° C., 0.500 mL of bromine was added and the cold bath was removed. After stirring for 1 hr, 40 mL of sodium bisulfite was added. The product was extracted into ether, dried, and concentrated. Chromatography on silica using 1:1 ethyl acetate and hexanes yielded 0.941 g (43%) of product, which was an oil. The product was analyzed by ultraviolet absorption, infrared spectroscopy, nuclear magnetic resonance spectroscopy, and mass spectrometry.

EXAMPLE 28

3-(2-Nitro-5-fluorophenyl)oxacyclopentan-2-one

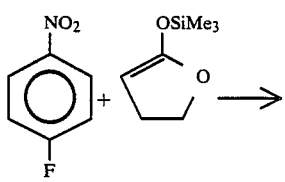

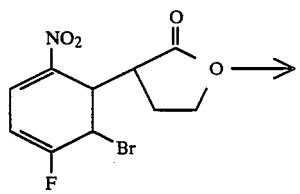

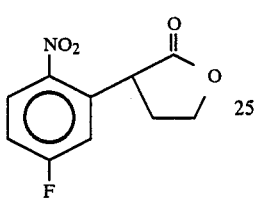

A. Using the procedure of Example 14, 4-fluoronitrobenzene (10 mmol) was substituted for nitrobenzene, and DFS 2 mL (10 mmol), was substituted for MTS. This yielded the ortho adduct exclusively, with 1.184 g (50%) ortho product produced. The melting point (EtOH) was 130° to 133° C. The product material was analyzed by ultraviolet absorption, infrared spectroscopy, nuclear magnetic resonance spectroscopy, and mass spectrometry.

B. To a flame-dried 500 mL round bottom flask equipped with magnetic stirrer, dropping funnel, and a thermocouple well, was added 5.30 mL (50 mmol) of 4-fluoronitrobenzene, 9.70 mL (52.5 mmol) of DFS and 250 mL of anhydrous THF. The mixture was cooled to −78° C., and 13.75 g of TASF (50 mmol) in 10 mL of anhydrous acetonitrile was added dropwise. Exothermic reaction occurred, and temperature was externally maintained below −75° C. The dropping funnel was rinsed with 5 mL of acetonitrile, and the solution was stirred for 30 min. The dry ice bath was removed, and the mixture was brought to −20° C. and further stirred for 1 hr. The solution was then cooled to −78° C., and 2.43 mL (48 mmol) of bromine in 25 mL of cyclohexane was added dropwise in 15 min. Stirring was continued for 10 min and the bath was removed. Fifty mL of saturated aqueous $KH_2PO_4$ was added, and the product extracted with three 50 mL portions of ether. Organic phase was washed with brine, dried over anhydrous magnesium sulfate, and concentrated. Column chromatography on silica using 1:1 ethyl acetate/hexane as solvent yielded 8.920 g (79.3%) of an off-white solid which was identified as the same product obtained in Part A.

EXAMPLE 29

Methyl α-Methyl-2-nitro-5-fluorophenyl-1-acetate

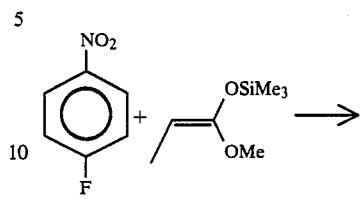

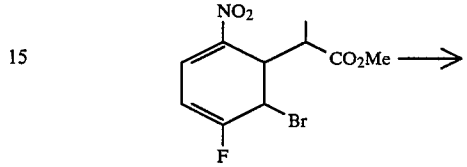

A. To a solution of 0.530 mL (5.00 mmol) of 4-fluoronitrobenzene and 1.11 mL (5.40 mmol) of MTS in 10 mL of anhydrous THF at −78° C. was added 1.3944 g (5.07 mmol) of TASF in 2 mL of acetonitrile and 2 mL of THF. The addition funnel was rinsed with 5 mL of THF. The mixture was stirred for 21 hrs at −78° C., and then 0.220 mL (4.30 mmol) of bromine was added. After being stirred at −78° C. for 15 min, the mixture was warmed to room temperature and stirring was continued for 30 min. Extraction with ether and chromatography on silica using 20% ether/hexane yielded the desired product. The yield was 0.479 (39%) of product, which was an oil. The product material was analyzed by infrared spectroscopy, nuclear magnetic resonance spectroscopy, and mass spectrometry.

B. The reaction of Part A was repeated except that the mixture was initially stirred at −15° to −20° C. for 1 hr instead of at −78° C. Sublimation of the ether extract yielded 6.100 g (77%) of the product. Structure was confirmed as in Part A.

C. The reaction of Part A was repeated except that tetra-n-butylammonium fluoride was substituted for TASF. The title product was obtained in 11% yield. Structure was confirmed by spectral comparison with the product of Part A.

EXAMPLE 30

2-(2-Nitro-5-fluorophenyl)-1-phenylethanone

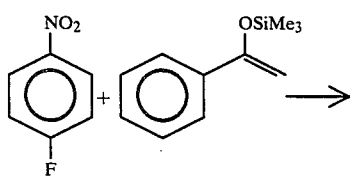

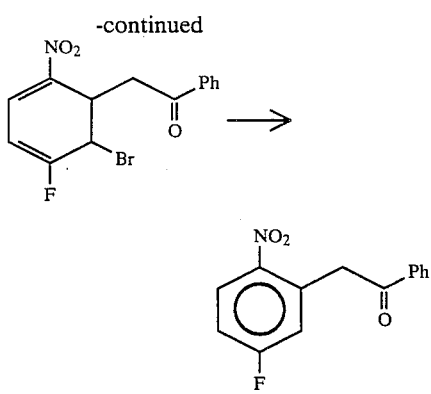

To a solution of 2.12 mL (20 mmol) of 4-fluoronitrobenzene and 4.12 mL (21 mmol) of [(1-phenyl-1-ethenyl)oxy]trimethylsilane in 30 mL of THF at −78° C. was added 5.502 g (20 mmol) of TASF dissolved in 6 mL of acetonitrile and 5 mL of THF. After stirring for 3 hrs at −78° C., 1.00 mL (19.50 mmol) of bromine in 5 mL of cyclohexane was added dropwise. After being stirred for 15 min at −78° C., the mixture was warmed to room temperature and stirred further for 30 min. Thirty mL of saturated sodium bisulfite was added, and the product was extracted into four 60 mL portions of ether. The organic phase was washed with saturated sodium chloride, dried, and concentrated. Chromatography on silica using 30% ether/hexanes yielded the expected product. The yield was 1.660 g (38%) of product, which was an oil. The product material was analyzed by infrared spectroscopy, nuclear magnetic resonance spectroscopy, and mass spectrometry.

EXAMPLE 31

Methyl α-Methyl-1-nitronaphthalene-2-acetate

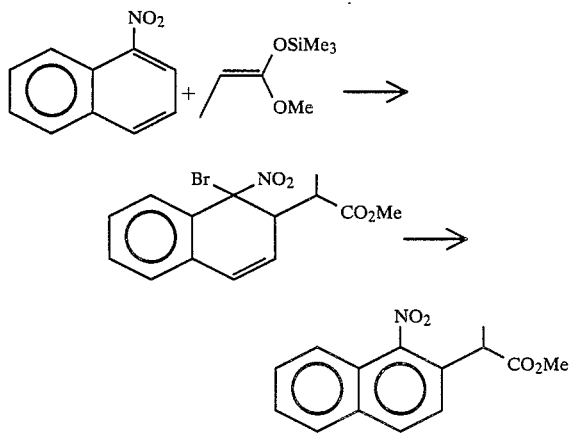

A solution of 1.375 g (5 mmol) of TASF in 5 mL of acetonitrile was added to a THF (15 mL) solution of 0.868 g (5 mmol) of 1-nitronaphthalene and 0.950 mL (5.05 mmol) of MTS at −78° C. The mixture was stirred overnight at −78° C. At −78° C., 0.240 mL (4.73 mmol) bromine was added, and the mixture was stirred for 15 min. Subsequently, the mixture was warmed to room temperature. Thirty mL of saturated sodium bisulfite was added, and the product was extracted with ether and filtered through a column of silica gel using ether/hexane as the solvent. Recrystallization of the crude product yielded 0.264 g (20%) of a colorless crystalline material identified as the nitro adduct. The melting point (EtOH) was 68° to 71° C. The following analytical data was used to determine the product's structure as depicted above: UV (EtOH): 360 (580), 319 (1130), 267 (5100), 223 (90650); IR (KBr): 3060, 1949, 1635, 1605, 1525, 1510, 1355 cm$^{-1}$; $^1$H NMR (360 MHz): δ 7.97 (d, J=8 Hz, 1H), 7.88 (d,m, J=8 Hz, 1H), 7.72 (d,m,J=8 Hz, 1H) 7.55–7.67 (m, 2H), 7.52 (d,J=10 Hz, 1H), 3.95 (q,J=7.0 Hz, 1H), 3.68 (s, 3H), 1.60 (d, J=7.0 Hz, 3H): HRMS: 259.0819 (M+; calculated for $C_{14}H_{13}NO_4$), 228.0668 (M+—OCH$_3$; calculated 228.0661), 213.0905 (M+—NO$_2$; calculated 213.0916).

EXAMPLE 32

3-(1-Nitronaphth-2-yl)oxacyclopentan-2-one

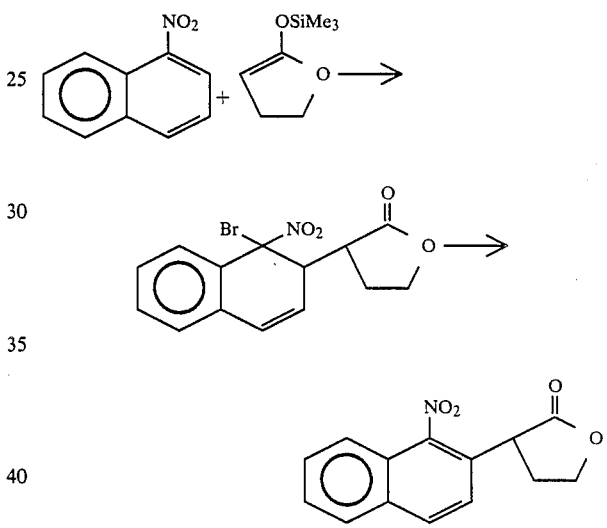

To a solution of 1.73 g (10 mmol) of 1-nitronaphthalene and 1.67 mL (10.5 mmol) of OCS in 30 mL of THF at −78° C. was added 2.751 g (10 mmol) of TASF dissolved in 5 mL of acetonitrile. The reaction mixture was brought to −10° C. (inside temp.), stirred for 1 hr, and subsequently cooled to −78° C. Bromine (0.510 mL, 10 mmol) in 5 mL cyclohexane was added. The bath was removed after 10 min, and the mixture was warmed to room temperature over 1 hr. Twenty-five mL of water was added, and the product was extracted with four 50 mL portions of ether. The combined organic phase was washed with 20 mL of water, dried, and concentrated. Column chromatography on silica using 20% ethyl acetate and hexane yielded 1.054 g (41%) of the adduct. A portion was recrystallized from methanol and the melting point was determined to be 149° to 152° C. The product was analyzed by ultraviolet absorption, infrared spectroscopy, nuclear magnetic resonance spectroscopy, and mass spectrometry.

EXAMPLE 33

Methyl α-Methyl-2-nitro-5-(2-chloro-2-propyl)-phenyl-1-acetate

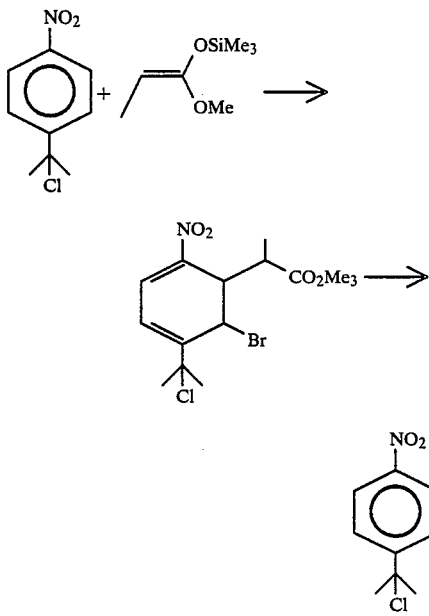

To a mixture of 0.814 mL (5.00 mmol) of 4-nitrocumylchloride and 0.933 mL (5.05 mmol) of MTS in 14 mL of anhydrous THF was added 1.376 g (5.00 mmol) of TASF in 10 mL of acetonitrile at −78° C. The mixture was stirred for 20 hrs at −78° C., and then 0.250 mL (5 mmol) of bromine in 5 mL of cyclohexane was added. Stirring was continued for 10 min at −78° C., and then the cold bath was removed. The reaction mixture was stirred at room temperature for 1 hr. Twenty mL of saturated aqueous sodium bisulfite was added, and the product was extracted into ether. Concentration followed by chromatography on silica using ether/hexane as the solvent yielded the product and uncovered starting material. The product yield was 0.446 g (31.2%). The product, an oil, was analyzed by infrared spectroscopy, nuclear magnetic resonance spectroscopy, and mass spectrometry.

EXAMPLE 34

Methyl α,α-Dimethyl-2-nitro-3-methoxy-5-chlorophenyl-1-acetate

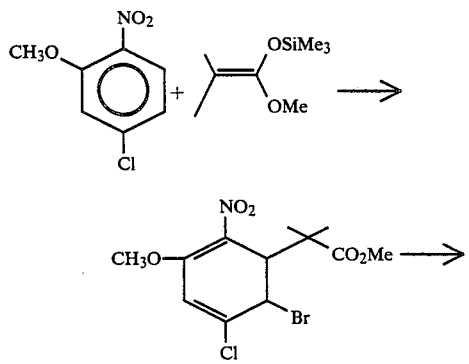

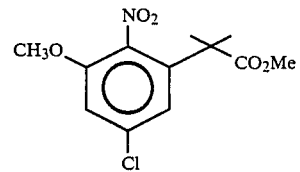

A flame-dried three-necked flask fitted with a dropping funnel and thermometer was charged with 1.51 g (8 mmol) of 2-nitro-5-chloroanisole and 2 mL (10 mmol) of MMTS in 30 mL of anhydrous THF. The addition funnel was charged with 2.20 g (8 mmol) of TASF in 5 mL of acetonitrile. After the contents of the flask was cooled to −78° C., the TASF solution was added slowly so that the temperature remained below −70° C. The mixture was warmed to −15° C. and stirred for 1 hr. A solution of 0.4 mL (8 mmol) of bromine in 5 mL of cyclohexane was added at −78° C. The cold bath was removed and the mixture was warmed to room temperature. Twenty mL of saturated potassium dihydrogen phosphate was added, and product was extracted into ether. The ether layer was dried over anhydrous magnesium sulfate and concentrated. The desired product was isolated by chromatography on silica using ethyl acetate/hexane as the solvent. The product yield was 1.5 g (65%). The melting point was 125° to 127° C. The product was analyzed by ultraviolet absorption, infrared spectroscopy, nuclear magnetic resonance spectroscopy, and mass spectrometry.

EXAMPLE 35

Methyl α,α-dimethyl-4-nitro-2,1,3-benzothiadiazole-5-acetate

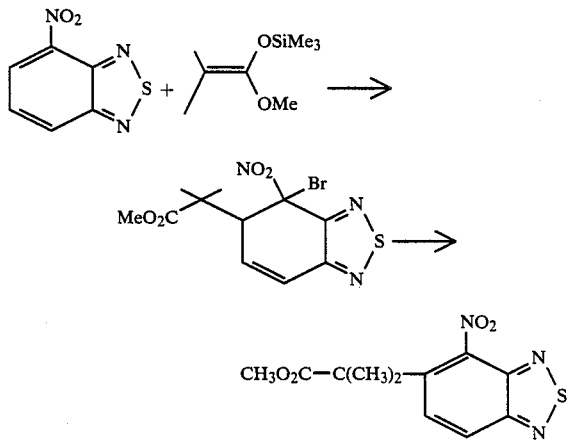

To 1.81 g (10 mmol) of 4-nitro-2,1,3-benzothiodiazole in 40 mL of anhydrous THF was added 2.14 mL (10.7 mmol) of MMTS, followed by 2.751 g (10 mmol) of TASF in 5 mL of acetonitrile at −10° C. The mixture was stirred for 1 hr at −10° C., and then 0.500 mL (9.76 mmol) of bromine in 5 mL of cyclohexane was added at −70° C. The reaction was allowed to come to room temperature and then worked up. Next, 1.800 g (64%) of the product was isolated by column chromatography on silica using ethyl acetate/hexane solvent system. The melting point was 134° to 136° C. The product was analyzed by infrared spectroscopy, nuclear magnetic resonance spectroscopy, and mass spectrometry.

EXAMPLE 36

Methyl 2-Nitro-3-Chlorophenyl-1-Acetate

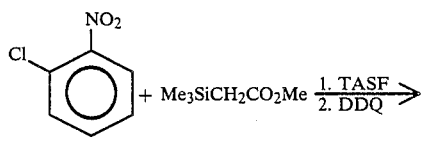
+ Me₃SiCH₂CO₂Me  $\xrightarrow{\text{1. TASF}}_{\text{2. DDQ}}$

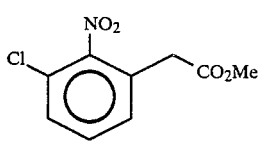

A. A mixture of 1.44 g (10 mmol) of 2-chloronitrobenzene and 1.57 mL of (carbomethoxymethyl)-trimethyl silane in 20 mL THF was treated with 2.75 g TASF in 3 mL dry acetonitrile at −70° C. After the temperature reached −40° C. (1 h), 2.3 g of dichlorodicyanoquinone (DDQ) dissolved in 20 mL THF was added, and the temperature was allowed to rise to room temperature. The product was extracted into ether after addition of 30 mL of water. The ether extract was washed with 1N sodium hydroxide, dried with anhydrous magnesium sulfate, and then concentrated. The product was isolated as an oil by column chromatography on silica gel using ether/petroleum ether as the solvent. The product yield was 1.16 g (51%). The structure of the product was confirmed by IR and NMR spectroscopy.

B. Following the procedure of Part A, the reactions summarized in Table 1 were carried out. Product structure was confirmed in each case by IR, NMR and mass spectrometry.

TABLE 1

| Ar in ArNO₂ | Silane | Formula II Product Ar³ | R² | R³ | R⁴ |
|---|---|---|---|---|---|
| Phenyl | [(cyclohex-1-ene)oxy]trimethylsilane | 1,2- and 1,4-phenylene | H | $-(CH_2)_4-$ | |
| 4-Chlorophenyl | Methyl 2-(trimethylsilyl)-acetate | 4-Chloro-1,2-Phenylene | H | H | OCH₃ |
| 2-Naphthyl | Methyl 2-(trimethylsilyl)-acetate | 1,2-Naphthylene | H | H | OCH₃ |
| 6-Aza-2-naphthyl | MTS | 6-Aza-1,2-naphthylene | H | CH₃ | OCH₃ |
| 4-(Cyclopropyl)phenyl | MTS | 4-(Cyclopropyl)-1,2-phenylene | H | CH₃ | OCH₃ |

EXAMPLE 37

Methyl 2-Methyl-1-nitronaphthalene-2-acetate and Methyl-2-methyl-1-naphthalene-2-acetate

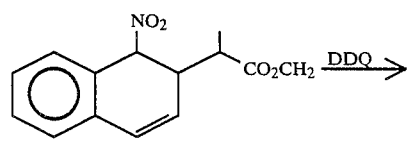 $\xrightarrow{\text{DDQ}}$

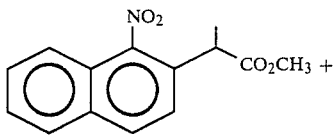

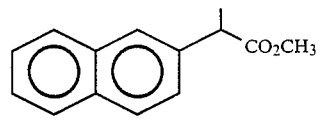

A solution of 0.50 g of 2-methyl-1-nitro-1,2-dihydronaphthalene-2-acetate and 0.70 g of DDQ in 20 mL of benzene was heated under reflux (approx. 80° C.) for 10 h. The products formulated above were isolated by column chromatography, and their structures confirmed by thin layer chromatography and NMR. The esters were converted by hydrolysis with 1N KOH in methanol/THF to the corresponding acetic acids. The denitrified product is a known anti-inflammatory agent disclosed in I. T. Harrison et al., *J. Med. Chem.*, 13, 203 (1970); and U.S. Pat. No. 3,637,767.

UTILITY EXAMPLE A

Methyl α,α-Diemthyl-4-aminophenyl-1-acetate

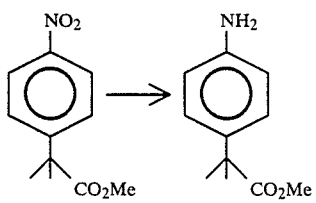

To 0.250 g of methyl α,α-dimethyl-4-nitrophenyl-1-acetate, prepared as in Example 16, in 5 mL of methanol, was added 0.360 g of tin granules. From the top of a condenser connected to the flask was added 2 mL of concentrated HCl, 0.3 mL at a time. After the addition was complete, the mixture was warmed on a water bath for 30 min. The mixture was cooled, and 10% aqueous sodium hydroxide was added to approximately pH 13. The product was extracted into ether, the combined ether layer was dried and concentrated. Chromatography using 20% acetone petroleum ether gave the product which was further identified as the benzoyl derivative. The melting point was 80° to 84° C. The product was analyzed by infrared spectroscopy, nuclear magnetic resonance spectroscopy, and mass spectrometry. The ester product can be hydrolyzed to the corresponding acetic acid by treatment with aqueous base, followed by acidification.

UTILITY EXAMPLE B

Methyl α,α-Dimethyl-3-methyl-4-aminophenyl-1-acetate

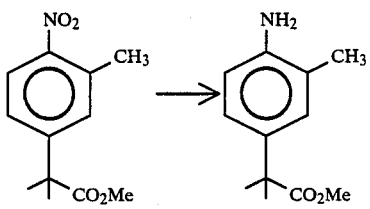

The method employed was that of Utility Example A, except that methyl α,α-dimethyl-3-methyl-4-nitrophenyl-1-acetate was used. The melting point was 69° to 70° C. The product material was analyzed by nuclear magnetic resonance spectroscopy. The ester product can be hydrolyzed to the corresponding acetic acid by treatment with aqueous base, followed by acidification.

UTILITY EXAMPLE C

3-Methyloxindole

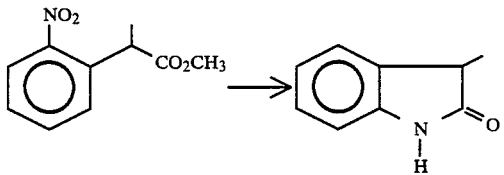

To 0.46 g of methyl α-methyl-2-nitrophenyl-1-acetate, prepared as in Example 17, in 5 mL of methanol was added 0.46 g of tin granules. From the top of a condenser connected to the flask was added 3 mL of concentrated HCl, 0.3 mL at a time. After the addition had been completed, the mixture was warmed on a water bath at 60° C. for 1 hr and 50 mL of 2N sodium hydroxide solution was added. After cooling to room temperature, the product was extracted into ether and the combined ether layer was dried, and concentrated. The product material was analyzed by infrared spectroscopy, nuclear magnetic resonance spectroscopy, and mass spectrometry.

UTILITY EXAMPLE D

3-Methyl-5,7-dichlorooxindole

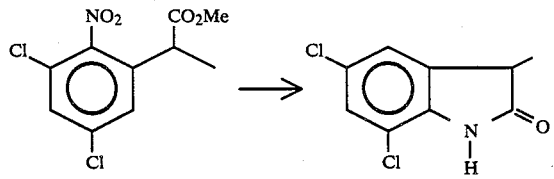

One g of methyl α-methyl-2-nitro-3,5-dichlorophenyl-1-acetate, prepared as in Example 25, was dissolved in 15 mL of 20% ethyl acetate and ethanol in a Parr bottle, and 200 mg of 10% palladium supported on carbon was added. The mixture was pressurized to 45 psi with hydrogen, and the reaction was continued until uptake of hydrogen ceased. The catalyst was filtered off with the aid of Celite and the product was isolated by chromatography on silica. The product was analyzed by infrared spectroscopy, nuclear magnetic resonance spectroscopy, and mass spectrometry.

UTILITY EXAMPLE E

3-Methyl-5-chlorooxindole

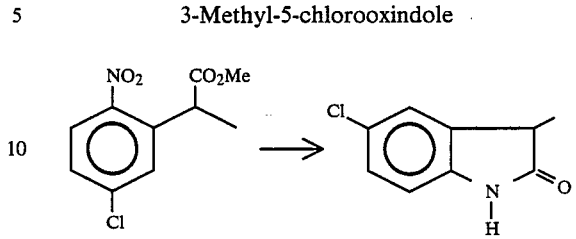

Using essentially the procedure of Utility Example D, the product was prepared from methyl α-methyl-2-nitro-4-chlorophenyl-1-acetate, prepared as in Example 22, and was analyzed by infrared spectroscopy, nuclear magnetic resonance spectroscopy, and mass spectrometry.

UTILITY EXAMPLE F

3-Methyl-5-methyloxindole

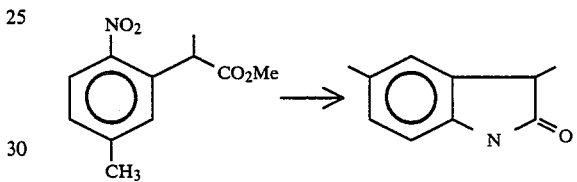

Using essentially the procedure of Utility Example D, the product was prepared from methyl α-methyl-2-nitro-5-metylphenyl-1-acetate. The intermediate nitro-aryl carbonyl compound preparation is described in Example 26. The product was analyzed by infrared spectroscopy, nuclear magnetic resonance spectroscopy, and mass spectrometry. It was determined that the product has the structure depicted above.

UTILITY EXAMPLE G

6-Chloro-1,2,3,4-tetrahydrocarbazole

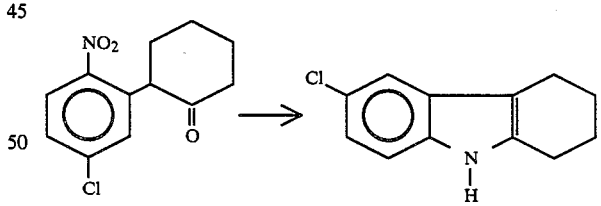

A. 0.600 g of 2-(2-nitro-5-chlorophenyl)cyclohexanone, prepared as in Example 21, was hydrogenated in a Parr hydrogenator using 100 mg of 10% Pd on C at 32 psi starting pressure of hydrogen. At the end of the reaction the catalyst was filtered off, and the product (0.483 g) was isolated by evaporation of the solvent and chromatography on silica using 1:4 $CCl_4/CH_2Cl_2$. The product was analyzed by infrared spectroscopy, nuclear magnetic resonance spectroscopy, and mass spectrometry.

B. The reduction can also be carried out using Fe/acetic acid. A mixture of 0.784 g of iron, 1.62 mL of glacial acetic acid, 0.544 g of sodium acetate, and 1 g of 2-(5-chloro-2-nitrophenyl)cyclo-hexanone was refluxed in 80 mL of 4:1 (v/v) ethanol/water for 2 hr. The mixture was cooled, ethanol was evaporated, and the residue was extracted into methylene chloride. Work-up followed by column chromatography on silica yielded 0.160 g (20%) of the named product.

UTILITY EXAMLE H

3-Hydroxyethyl-5-fluoroindole

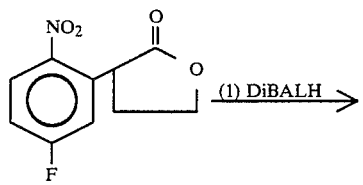

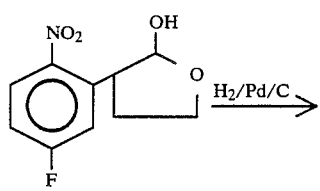

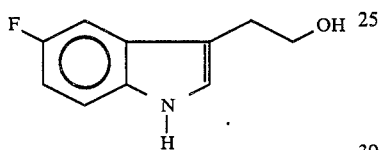

To 75 mL of an anhydrous THF solution of 2.25 g (10 mmol) of 3-(2-nitro-5-fluorophenyl)oxacyclopentan-2one, prepared as in Example 28, at −30° C., was added 12 mL of 1M diisobutyl aluminum hydride solution over 5 min. The mixture was stirred for 2 hr at −30° C., 20 mL of sodium potassium tartrate was added, and the mixture was further stirred for 30 min. Extraction with ether, drying over magnesium sulfate and concentration yielded 2.23 g (98%) of product which was purified by column chromatography. GLPC indicated this to be a mixture of diastereomers (3% SP2100 on Supelcoport 6′×⅛′ glass column). The product was analyzed by infrared spectroscopy, nuclear magnetic resonance spectroscopy, and mass spectrometry.

This product was further reduced with Pd/C/H$_2$, as illustrated in Utility Example D, to obtain 3-hydroxyethyl-5-fluorooxindole. Recrystallization of the fluorooxindole yielded 98% product with a melting point of 89° to 91° C. The product was analyzed and identified by infrared spectroscopy, nuclear magnetic resonance spectroscopy, and mass spectroscopy.

What is claimed is:

1. A process for making a nitroaryl carbonyl compound of the formula

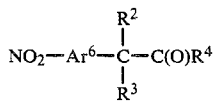

comprising (a) mixing a nitroaryl compound of the formula

Ar$^4$NO$_2$ with a silane of the formula

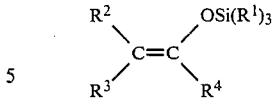

under anhydrous conditions: (b) cooling the mixture to a temperature below about −20° C.; (c) adding a fluoride-containing compound that will provide fluoride ions under reaction conditions, said compound selected from tris(dialkylamino)sulfonium difluorotrimethylsilicate and tetra n-butylammonium fluoride; (d) adding a proton-containing compound that will provide under reaction conditions an electrophilic compound to form an intermediate nitrodihydroaryl carbonyl compound of the formula

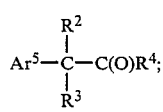

said proton-containing compound selected from the group consisting of water, an acidic salt, a mineral acid or a carboxylic acid; (e) isolating the intermediate from the mixture; (f) dissolving the intermediate in a solvent; and (g) treating the intermediate with a quinone; wherein:

R$^1$, individually, is C$_{1-4}$ alkyl or phenyl, provided that no more than one of R$^1$ is phenyl;

R$^2$ and R$^3$, individually, are H, C$_{1-12}$ hydrocarbyl, C$_{2-12}$ heteroacyclic radical or C$_{3-8}$ heterocyclic radical, wherein the heteroatoms are selected from ether oxygen and tertiary nitrogen;

R$^4$ is C$_{1-12}$ hydrocarbyl or C$_{1-12}$ hydrocarbyloxy; or

R$^3$ and R$^4$ can be taken together to form a member of the group CH$_2$CH$_2$O, (CH$_2$)$_n$, and CH$_2$CH$_2$N(CH$_3$)CH$_2$ when R$^2$ is H;

n is 4, 5, or 6;

Ar$^4$ is an aryl radical selected from 2-thienyl; 6-aza-1-naphthyl; 1-naphthyl; 9 anthryl; and substituted derivatives thereof; wherein said substituents are inert under reaction conditions;

Ar$^5$ is a nitrodihydroaryl radical selected from

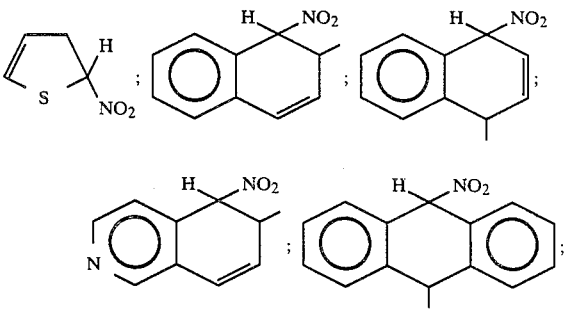

and substituted derivatives thereof, wherein said substituents are inert under reaction conditions; and Ar$^6$ is a divalent radical selected from

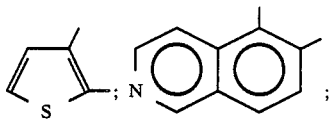

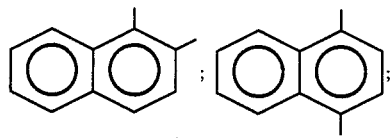

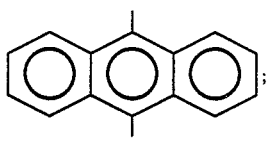

and substituted derivatives thereof, wherein said substituents are inert under reaction conditions.

2. A process according to claim 1 wherein the solvent of step (f) is an aromatic hydrocarbon.

3. A process according to claim 2 wherein the aromatic hydrocarbon is toluene, xylene or benzene.

4. A process according to claim 1 wherein the quinone is tetrachloro-1,4-benzoquinone, tetrachloro-1,2-benzoquinone or 2-3-dichloro-5,6-dicyano-1,4-benzoquinone.

5. A process according to claim 1 wherein step (g) further comprises heating the treated intermediate to a temperature of about 50° to 150° C.

6. A process according to claim 5 wherein the temperature is 80° to 100° C.

7. A process according to claim 1 wherein the quinone is present in a molar ratio of about 1 to 3 with respect to the intermediate present.

8. A process according to claim 1 wherein the silane is ((1-methoxy-2-methyl-1-propenyl)oxy)trimethylsilane, ((1-methoxy-1-propenyl)oxy)trimethylsilane, (carbomethoxymethyl)trimethylsilane or ((oxacyclopent-2-ene-2-yl)oxy)trimethylsilane.

9. A process according to claim 1 wherein the fluoride ion source is a compound which will produce fluoride ions under reaction conditions.

10. A process according to claim 9 wherein the fluoride ion source is at least partially soluble in the solvents employed.

11. A process according to claim 10 wherein the fluoride ion source is tris(dimethylamino)sulfonium difluorotrimethylsilicate or tetra n-butylammonium fluoride.

12. A process according to claim 1 wherein the proton source is water, an acidic salt, or an acid.

13. A process according to claim 12 wherein the acid is a mineral acid or a carboxylic acid.

14. A process according to claim 13 wherein the acid is hydrochloric acid or glacial acetic acid.

15. A process according to claim 1 wherein step (a) further comprises adding a polar aprotic solvent.

16. A process according to claim 15 wherein the polar aprotic solvent is tetrahydrofuran; acetonitrile; an ether; a glycol ether such as tetraglycol dimethylether; dimethylformamide; pyridine or a mixture thereof.

17. A process according to claim 16 wherein the polar aprotic solvent is a mixture of tetrahydrofuran and acetonitrile.

18. A process according to claim 17 wherein the mixture is cooled to a temperature below −70° C. during step (b).

19. A process according to claim 1 wherein step (d) is operated at a temperature of 0° C. or below.

20. A process according to claim 1 wherein the nitroaryl compound is polynuclear; the solvent of step (f) is toluene, xylene or benzene; the quinone is tetrachloro-1,4-benzoquinone, tetrachloro-1,2-benzoquinone or 2-3-dichloro-5,6-dicyano-1,4-benzoquinone; step (g) further comprises heating the treated intermediate to a temperature of 80° to 100° C.; the quinone is present in a molar ratio of about 1 to 3 with respect to the intermediate present; the silane is ((1-methoxy-2-methyl-1-propenyl)oxy)trimethylsilane; the fluoride ion source is tris(dimethylamino)sulfonium difluorotrimethylsilicate; the proton source is hydrochloric acid or glacial acetic acid; step (a) further comprises adding a mixture of tetrahydrofuran and acetonitrile as a polar aprotic solvent; the mixture is cooled to a temperature below −70° C. during step (b); and step (d) is operated at a temperature of 0° C. or below.

* * * * *